US007691858B2

(12) United States Patent
Doukas et al.

(10) Patent No.: US 7,691,858 B2
(45) Date of Patent: Apr. 6, 2010

(54) KINASE INHIBITORS AND METHODS OF USE THEREOF

(75) Inventors: John Doukas, San Diego, CA (US); Chi Ching Mak, San Diego, CA (US); Elena Dneprovskaia, San Diego, CA (US); Glenn Noronha, Oceanside, CA (US)

(73) Assignee: TargeGen, Inc., San Diego, CA (US)

( * ) Notice: Subject to any disclaimer, the term of this patent is extended or adjusted under 35 U.S.C. 154(b) by 42 days.

(21) Appl. No.: 11/789,832

(22) Filed: Apr. 25, 2007

(65) Prior Publication Data

US 2007/0259876 A1 Nov. 8, 2007

Related U.S. Application Data

(60) Provisional application No. 60/795,218, filed on Apr. 25, 2006.

(51) Int. Cl.
C07D 475/08 (2006.01)
C07D 241/20 (2006.01)
C07D 241/12 (2006.01)
C07D 241/24 (2006.01)
A61K 31/4985 (2006.01)
A61P 9/08 (2006.01)
A61P 11/00 (2006.01)
A61P 35/00 (2006.01)
A01N 43/50 (2006.01)

(52) U.S. Cl. .................. 514/249; 544/260; 544/407; 544/336; 544/409

(58) Field of Classification Search .............. 544/260; 514/249

See application file for complete search history.

(56) References Cited

U.S. PATENT DOCUMENTS

| 2,667,486 | A | 1/1954 | Cain |
| 4,057,530 | A | 11/1977 | Pigerol et al. |
| 5,214,059 | A | 5/1993 | Tegeler et al. |
| 5,597,901 | A | 1/1997 | Stern |
| 5,776,502 | A | 7/1998 | Foulkes et al. |
| 5,830,880 | A | 11/1998 | Sedlacek et al. |
| 6,070,126 | A | 5/2000 | Kokolus et al. |
| 6,121,434 | A | 9/2000 | Peyman et al. |
| 6,136,779 | A | 10/2000 | Foulkes et al. |
| 6,194,191 | B1 | 2/2001 | Zhang et al. |
| 6,204,260 | B1 | 3/2001 | Bruns, Jr. et al. |
| 6,326,487 | B1 | 12/2001 | Peyman et al. |
| 6,348,312 | B1 | 2/2002 | Peyman et al. |
| 6,471,968 | B1 | 10/2002 | Baker, Jr. et al. |
| 6,489,328 | B2 | 12/2002 | Snow et al. |
| 6,506,769 | B2 | 1/2003 | Snow et al. |
| 6,635,626 | B1 | 10/2003 | Barrish et al. |
| 6,685,938 | B1 | 2/2004 | Cheresh et al. |
| 6,689,778 | B2 | 2/2004 | Bemis et al. |
| 7,208,493 | B2 | 4/2007 | Wrasidlo et al. |
| 7,230,101 | B1* | 6/2007 | Murthi et al. ............ 544/260 |
| 2005/0245524 | A1 | 11/2005 | Noronha et al. |
| 2005/0282814 | A1 | 12/2005 | Wrasidlo et al. |
| 2006/0079526 | A1 | 4/2006 | Wrasidlo et al. |
| 2006/0247250 | A1 | 11/2006 | Cao et al. |
| 2006/0292203 | A1 | 12/2006 | Dellamary et al. |
| 2007/0149508 | A1 | 6/2007 | Noronha et al. |
| 2007/0161645 | A1 | 7/2007 | Noronha et al. |
| 2007/0191405 | A1 | 8/2007 | Noronha et al. |
| 2007/0208019 | A1 | 9/2007 | Wrasidlo et al. |
| 2007/0259876 | A1 | 11/2007 | Doukas et al. |
| 2007/0259904 | A1 | 11/2007 | Noronha et al. |
| 2008/0027070 | A1 | 1/2008 | Noronha et al. |

FOREIGN PATENT DOCUMENTS

| EP | 0059524 | 9/1982 |
| FR | 2275461 | 1/1976 |
| GB | 1149640 | 4/1969 |
| WO | WO-/97/21711 | 6/1997 |
| WO | WO-/00/39129 | 7/2000 |
| WO | WO-01/53266 | 7/2001 |
| WO | WO-02/097116 | 12/2002 |
| WO | WO-2004/005283 | 1/2004 |
| WO | WO-2004/032709 | 4/2004 |
| WO | WO-2004/037814 | 5/2004 |

OTHER PUBLICATIONS

Jacquet, et al., J. Sep. Sci. 2004, 27, 1221-1228.*
Bell, et al., J. Molec. & Cellul. Cardiol., vol. 35, # 2, Feb. 2003, 185-193.*
Assmus, et al., Circulation Research, May 16, 2003, 1049-1055.*
Nienaber, et al., J. Clin. Invest. 112(7): 1067-1079 (2003).*
Liu, et al., J. Biol. Chem., vol. 283, # 15, 9977-9985, Apr. 11, 2008.*
Wikipedia, Wortmannin, <http://en.wikipedia.org/wiki/Wortmannin>, updated Jan. 22, 2009, downloaded Feb. 4, 2009.*
De la Pena, et al., Mol Cancer Ther. 2006;5:1504-1510.*
Bolen et al., "Expression and interaction of the SRC family of tyrosine protein kinases in T lymphocytes", Adv. Cancer Res., vol. 57., 103-149, PMID 1950702, 1991.
Chawla et al., "Challenges in Polymorphism of Pharmaceuticals", CRIPS, vol. 5, No. 1, Jan.-Mar. 2004 (4 pages).
Frohlich et al., "Inhibition of Neuronal Nitric Oxide Synthase by 4-Amino Pteridine Derivatives: Structures-Activity Relationship of Antagonists of (6R)-5,6,7,8-Tetrahydrobiopterin Cofactor", J. Med. Chem., vol. 42, 4108-4121, 1999.

(Continued)

Primary Examiner—Mark L Berch
Assistant Examiner—Cecilia M Jaisle
(74) Attorney, Agent, or Firm—Goodwin Procter LLP

(57) ABSTRACT

Compositions and methods and are provided for treating disorders associated with compromised vasculostasis. Invention methods and compositions are useful for treating a variety of disorders including for example, stroke, myocardial infarction, cancer, ischemia/reperfusion injury, autoimmune diseases such as rheumatoid arthritis, eye diseases such as uveitis, retinopathies or macular degeneration, macular edema or other vitreoretinal diseases, inflammatory diseases such as autoimmune diseases, vascular leakage syndrome, edema, or diseases involving leukocyte activation, transplant rejection, respiratory diseases such as asthma, adult or acute respiratory distress syndrome (ARDS), chronic obstructive pulmonary disease, and the like.

7 Claims, 4 Drawing Sheets

OTHER PUBLICATIONS

Granelli-Piperno, "SRC-related proto-oncogenes and transcription factors in primary human T cells; modulation by cyclosporine A and FK506", J. Autoimmun., vol. 5, Suppl. A, 145-148, PMID.

Jacobson, et al., Am. J. Physiol. Lung Cell Mol. Physiol, 288, 1026-1032.

Kobayashi et al., "Functional coupling of the src-family protein tyrosine kinases p59fyn and p53/56 lyn with the interleukin 2 receptor: implications for redundancy and pleiotropsim in cytokine signal transduction", Proc. Natl. Acad. Sci., USA, vol. 1:90, No. 9, 4201-4205, Abstract, PMID 8483935, May 1993.

New Mexico Department of Health, Interluekin-2, http://www.aidsinfonet.org, Project of the New Mexico Aids Education and Training Center, Fact Sheet No. 6232, Apr. 30, 2002.

Newman et al., "Solid-state Analysis of the Active Pharmaceutical Ingredient in Drug Products", DDT, vol. 8, No. 19, Oct. 2003, p. 898-905.

O'Shea et al., "Expression of v-src in a Murine T-cell Hybridoma Results in Constitutive T-cell Receptor Phosphorylation and Interleukin 2 Production", Proc. Natl. Acad. Sci., 88:1741-1745 (1991).

Taghavi-Moghadam et al. "A New, General and Regioselective Method for the Syntehsis of 2,6-Disubstituted 4-Aminopteridines", Elsevier Science Ltd., Pergamon, 6835-6836, 1997.

Tanaka et al., "novel human tyrosine kinase gene inducible in T cells by interleukin 2", Febs Lett., vol. 7:324, No. 1, 1-5, PMID 9504851, Jun. 1993.

Torigoe et al., "Regulation of SRC-family protein tyrosine kinases by interleukin, IL-2, and IL-3", Leukemia, vol. 6, Supplemental 3, 94S-97S, PMID 1602836, 1992.

Weber, "Molecular Approaches to Study Cellular Roadblocks to Transfections and Transduction (Non-Viral Vectors and AAV-Based Vectors for Gene Therapy)", http//www.mssm.edu/genetherapy/weber.htm, 1-8, Nov. 11, 2002.

Wills, et al., The New England Journal of Medicine, 2005, 353, 9, 877-889.

Yamamoto et al., "Role of src-like protooncogenes in lymphocotye proliferation", Princess Takamastu Symp., vol. 22, 293-305 Review, PMID 1668889, 1991.

http://en.wikipedia.org/wiki/Acute_respiratory_distress_syndrome.

http://en.wikipedia.org/wiki/Myocardial_infarction, Myocardial Infarction.

http://www.emedicinehealth.com/acute_respiratory_distress_syndrome.

http://www.majoclinic.com/health/stroke/DS00150/SECTION=7.

http://www.medscape.com/viewarticle/544205_print.

International Search Report for PCT Application No. PCT/US2003/031721.

European Search Report for European Application No. EP 03 77 4610.

* cited by examiner

KINASE INHIBITORS AND METHODS OF USE THEREOF

CROSS REFERENCE TO RELATED APPLICATIONS

This application claims the benefit under 35 USC §119(e) of U.S. Application Ser. No. 60/795,218 filed Apr. 25, 2006. The disclosures of the prior application is considered part of, and incorporated by reference in, the disclosure of this application.

FIELD OF THE INVENTION

The present invention relates generally to kinase inhibitors and lipid kinase inhibitors and more specifically to phosphoinositide kinase inhibitors and methods of use for such inhibitors in attenuating the effects of compromised vasculostasis, and further in treating disorders associated with cardiovascular diseases, cancers, ocular diseases, respiratory diseases, inflammatory disease and diseases involving deleterious or unwanted angiogenesis.

BACKGROUND OF THE INVENTION

The vascular system is a prime mediator of homeostasis, playing key roles in the maintenance of normal physiologic functioning. For example, the vascular endothelium's barrier function serves to regulate the entry of fluid, electrolytes, and proteins into tissues, blood vessel tone contributes to the regulation of tissue perfusion, and the vascular endothelium's low mitotic index contributes to the regulation of tissue growth. The term "vasculostasis" refers to the maintenance of this homeostatic vascular functioning, and "vasculostatic agents" as agents that seek to address conditions in which vasculostasis is compromised by preventing the loss of or restoring or maintaining vasculostasis.

Compromised vasculostasis has serious pathologic consequences. For example, if vascular permeability increases beyond manageable levels, the resulting edema may negatively impact tissue and organ function and ultimately survival. Examples where excessive vascular permeability leads to particularly deleterious effects include pulmonary edema, cerebral edema, and cardiac edema (Ritchie A C: *Boyd's Textbook of Pathology*. London Lea and Febiger, 1990). In general, however, edema in any tissue or organ leads to some loss of normal function, and therefore to the risk of morbidity or even mortality. Similarly, excessive endothelial proliferation may damage tissues (such as the retina in proliferative retinopathies) or fuel unwanted tissue growth (such as with tumor growth).

Many pathologic and disease situations are marked by multiple disregulations in vasculostasis. Angiogenesis, for example, encompasses both enhanced vascular proliferation and permeability, as newly-formed blood vessels do not generally exhibit the same level of vascular barrier function as well-established or mature vessels. Examples of such hyperpermeable vasculature can be found in cancers, vasculoproliferative diseases, retinal diseases, and rheumatoid arthritis. The connection between angiogenesis and hyperpermeability may partly result from the dual action of factors such as vascular endothelial growth factor (VEGF), which induces both endothelial proliferation and vascular permeability. This connection may also reflect the immature nature of angiogenic vessels, in which the intracellular and/or extracellular structures or mechanisms that establish normal vascular barrier function have not yet fully formed. It may also be the case that angiogenesis and vascular permeability are linked by a co-dependence on common cellular mechanisms, for example in the case of cellular junction disassembly which would serve to enhance both paracellular permeability and cellular migration (both being components of the angiogenic process). A comprehensive treatment for many diseases, then, might involve vasculostatic agents that act upon one or more components of vasculostasis disregulation (based, for example, upon their level of action along intracellular signaling cascades). One such example would be a single therapeutic agent that impacts both angiogenesis and vascular permeability.

One way of impacting vasculostasis is by influencing endothelial cell responses to environmental signals (such as hypoxia) or vasoactive agents. For example, the vascular endothelium regulates fluid balance by adjusting both transcellular permeability (movement of fluid and proteins across endothelial cells via a network of vesicles) and paracellular permeability (movement of fluid and proteins between inter-endothelial cell junctions). Edema is most commonly thought to result from a breakdown in the inter-endothelial cell barrier, leading to increased paracellular permeability at the capillary and postcapillary venule level. Mechanistically, paracellular vascular leakage results from a breakdown in intercellular junctional integrity, via the dissolution of tight junctions and coupled to changes in cytoskeletal support elements that maintain normal cell-to-cell apposition. Several vasoactive mediators can trigger dissolution of these cellular elements, including histamine, bradykinin, thrombin, nitric oxide, eicosanoids (e.g., thromboxanes and leukotrienes), platelet activating factor (PAF), tumor necrosis factor (TNF), interleukins (e.g., IL-1 and IL-6), hepatocyte growth factor (HGF), and vascular endothelial growth factor (VEGF). Using VEGF as an example, the sequence of events that lead to vascular leakage is generally believed to be as follows: reduced blood flow (e.g., as a result of thrombus formation) leads to tissue hypoxia, which leads to the upregulation of VEGF production, which leads to induction of vascular leakage. This VEGF effect is at the level of the endothelial cell, in other words VEGF binding to specific VEGF receptors expressed on endothelial cells leads to a cascade of intracellular events culminating in the loss of normal intercellular barrier function. Therefore, by affecting these intracellular events, vasulostatic agents could counter the negative effects of environmental signals such as hypoxia or vasoactive mediators such as VEGF, and thereby work to restore vasculostasis.

The cascade of events that leads to the loss of endothelial barrier function is complex and incompletely understood. Data support a role for kinases as at least one aspect of this process. For example, VEGF-mediated edema has been shown to involve intracellular signaling by Src family kinases, protein kinase C, and Akt kinase. Kinases are believed to mediate the phosphorylation of junctional proteins such as beta-catenin and vascular endothelial (VE)-cadherin, leading to the dissolution of adherens junctions and the dissociation of cadherin-catenin complexes from their cytoskeletal anchors. In addition, proteins which regulate the intercellular contractile machinery such as myosin light chain kinase (MLCK) and myosin light chain (MLC) are also activated, resulting in cellular contraction, and therefore an opening of intercellular junctions.

One group of signaling molecules involved in regulating vascular function is the phosphotidylinositol 3-kinase (PI3K) family of kinases. Several isoforms of PI3K exist and are divided into classes based on structural and activity similarities. PI3K family members are key components of the intracellular signaling cascades triggered by both growth factor and G protein-coupled receptors (e.g., VEGF and histamine receptors). As such, they have been shown to mediate such endothelial-based activities as the regulation of vascular barrier function. Additionally, PI3K family members are also key mediators of leukocyte functioning, including activities such as migration into tissues and cytokine production. As would be predicted, then, the PI3K family plays an important role in inflammatory responses. Therefore, in addition to direct roles in regulating vasculostasis, the PI3K family can also influence situation in which vasculostasis is compromised (including ischemia and ischemia-reperfusion injury) through their control of leukocyte functioning.

Maintaining or restoring vasculostasis should be beneficial to overall patient outcome in situations such as inflammation, allergic diseases, cancer, cerebral stroke, myocardial infarction, pulmonary and cardiac insufficiency, renal failure, and retinopathies, to name a few. In addition, edema formation is a recognized but unwanted consequence of many therapeutic interventions, such as immunotherapy, cancer chemotherapy and radiation therapy, therefore vasculostatic agents that inhibit vascular permeability could be used in a co-therapy approach to reduce the deleterious side-effects of such therapies. Furthermore, in many cases edema formation causes uneven delivery of therapeutic agents to diseased tissues, therefore vasculostatic agents that inhibit vascular permeability could be used in a co-therapy approach to enhance delivery and efficacy of such therapies. Finally, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) or physical trauma, could be treated both acutely and prophylactically using vasculostatic agents that reduce vascular permeability.

Myocardial infarction (MI) results from a biphasic ischemia/reperfusion (I/R) injury to the heart, initiating with cardiomyocyte apoptosis then proceeding to a second wave of inflammation-based tissue damage. Despite considerable effort, therapeutic interventions to disrupt this injury pattern have not translated well from preclinical studies into the clinic. One major limitation has been a focus on anti-ischemia therapies that require delivery early in MI pathogenesis, a time when the great majority of patients are inaccessible. By contrast, while reperfusion injury does unfold in the appropriate interventional setting, inflammation's multifactorial nature complicates attempts to limit its impact. For example, pro-inflammatory mediators generated during I/R injury include vascular endothelial growth factor (VEGF), platelet activating factor (PAF), multiple cytokines and eicosanoids, histamine, thrombin and complement factors. While this diversity makes blockade at the receptor level unfeasible, inhibition at the sub-receptor level would be reasonable were a common signaling element identifiable.

Shock is often a life threatening medical or surgical condition in which a patient presents with an insufficiency of blood circulation leading to inadequate blood flow to vital organs and subsequent ischemia. Hemorrhagic and hypovolemic shock may lead to several medical emergencies which may include cardiac arrest, myocardial infarction (MI), organ failure and distress or failure of respiratory function. Shock arising from adverse heart conditions such as (MI) is typically termed cardiogenic shock and arises from blockage of blood flow to or from the heart, acute loss of fluids and ischemia to cardiac tissues. Several consequences of shock may include sepsis, anaphylaxis, inflammation, vascular permeability and distress or failure of neurological capacity. In some acute cases, septic shock results in a mortality rate of between 30-50%.

Phosphoinositide 3-kinase (PI3K) could represent this gatekeeper, lying downstream of both receptor tyrosine kinases (RTK) and G protein-coupled receptors (GPCR), two receptor classes encompassing the ligands listed above. Although phosphoinositide 3-kinases (PI3K) play beneficial pro-cell survival roles during tissue ischemia, some isoforms ($\gamma$ and $\delta$) paradoxically contribute to the inflammation that damages these same tissues upon reperfusion.

SUMMARY OF THE INVENTION

The present invention is based on the discovery that certain chemical compounds are effective in inhibiting phosphoinositide 3-kinases, most specifically the PI3K$\gamma$/$\delta$ isoforms. Such compounds are useful in treating cardiovascular diseases (heart conditions and injury to cardiac tissues following myocardial infarction and reperfusion, for example), cancer and related processes (solid tumor growth, tumor metastases, leukemis, pleural effusions), ocular diseases (glaucoma, uveitis, age-related macular degeneration, diabetic retinopathy, retinopathy of prematurity, macular edema), respiratory diseases (asthma, acute or adult respiratory distress syndrome, chronic obstructive pulmonary disease), inflammatory diseases (autoimmune disease, diseases involving edema, diseases involving leuckocyte activation) and diseases involving unwanted or deleterious angiogenesis. Compositions and methods are also provided for treating disorders associated with compromised vasculostasis, examples of which are edema resulting from excess vascular permeability or vascular leakage and angiogenesis associated with retinal diseases, cancers, inflammatory diseases, respiratory diseases and ocular diseases. Some of the compounds described herein are effective kinase inhibitors, including but not limited to lipid, tyrosine, serine or threonine kinase inhibitors, for example, phosphoinositide kinases including various classes and sub-classes.

Such vasculostatic agents, alone or in combination with other agents, are effective in blocking vascular permeability or leakage or angiogenesis. In one embodiment, the invention provides a composition containing a therapeutically effective amount of a compound of the invention in a pharmaceutically acceptable carrier.

In one embodiment, the invention provides a method for treating a disorder associated with compromised vasculostasis in a subject, comprising administering to a subject in need thereof an effective amount of a compound that is a vasculostatic agent. In an illustrative example, the method includes use of at least one of the compounds as set forth in Structure A. In specific aspects, the compound is exemplified as shown in Compound I, II, or III.

In one embodiment, the invention provides a method for treating a disorder associated with compromised vasculostasis, comprising administering to a subject in need thereof an effective amount of a compound, wherein the compound is set forth in Structure A. In one aspect, an illustrative compound of Structure A is shown as Compound II or III, wherein the compound may be 3-(2,4-diaminopteridin-6-yl)phenol or 6-(1H-Indol-4-yl)pteridine-2,4-diamine, respectively. The disorder is for example, but not limited to, myocardial infarction, stroke, congestive heart failure, an ischemia or reperfusion injury, cancer, arthritis or other arthropathy, retinopathy or vitreoretinal disease, macular degeneration, autoimmune disease, respiratory diseases, vascular leakage syndrome, inflammatory disease, edema, hypovolemic and hemorrhagic shock, chronic obstructive pulmonary disorder, transplant rejection, burn, or acute or adult respiratory distress syndrome (ARDS). In specific aspects, the compound is exemplified as shown in Compound I, II, or III.

In still another embodiment, there are provided articles of manufacture including packaging material and a pharmaceutical composition contained within the packaging material, wherein the pharmaceutical composition is capable of treating a disorder associated with compromised vasculostasis, wherein the pharmaceutical composition comprises at least one compound, such as Compound II or III.

In one embodiment, the invention provides a pharmaceutical composition comprising a compound as set forth in Structure A, such as Compound II or III in a pharmaceutically acceptable carrier.

In one embodiment, the invention provides an article of manufacture comprising packaging material and a pharmaceutical composition contained within said packaging material, wherein said packaging material comprises a label which indicates that said pharmaceutical composition can be used for treatment of disorders associated with compromised vasculostasis and wherein said pharmaceutical composition comprises a compound set forth in Structure A, such as Compound II or III.

In one embodiment, the invention provides an article of manufacture comprising packaging material and a pharmaceutical composition contained within said packaging material, wherein said packaging material comprises a label which indicates that said pharmaceutical composition can be used for treatment of disorders associated with vascular permeability leakage or compromised vasculostasis selected from is myocardial infarction, stroke, congestive heart failure, an ischemia or reperfusion injury, cancer, arthritis or other arthropathy, retinopathy or vitreoretinal disease, macular degeneration, autoimmune disease, respiratory diseases, vascular leakage syndrome, inflammatory disease, edema, hypovolemic and hemorrhagic shock, chronic obstructive pulmonary disorder, transplant rejection, burns, or acute or adult respiratory distress syndrome (ARDS) and wherein said pharmaceutical composition comprises a compound set forth in Structure A, such as Compound II or III.

In one embodiment, the invention provides a method of treating a compromised vasculostasis disorder, comprising the administration of a therapeutically effective amount of at least one compound set forth in Structure A, such as Compound II or III, in pharmaceutically acceptable N-oxides, salts, hydrates, solvates, crystal forms and individual diastereomers thereof, to a subject in need of such treatment.

In one embodiment, the invention provides a method of treating a disorder associated with vasculostasis, comprising the administration of a therapeutically effective amount of at least one compound as set forth in Structure A, such as Compound II or III, in pharmaceutically acceptable N-oxides, salts, hydrates, solvates, crystal forms and individual diastereomers thereof, in combination with an anti-inflammatory, chemotherapeutic agent, immunomodulatory agent, therapeutic antibody or a lipid kinase inhibitor, to a subject in need of such treatment.

In one embodiment, the invention provides a method of treating a subject having or at risk of having myocardial infarction comprising administering to the subject a therapeutically effective amount of a compound as set forth in Structure A, such as Compound II or III, thereby treating the subject. In addition, the method includes administration of an inhibitor of a PI3K family member, such as LY294002, for example.

In one embodiment, the invention provides a method of treating a subject having or at risk of having vascular leakage syndrome (VLS) comprising administering to the subject a therapeutically effective amount of a compound as set forth in Structure A, such as Compound II or III, thereby treating the subject.

In one embodiment, the invention provides a method of treating a subject having or at risk of having cancer comprising administering to the subject a therapeutically effective amount of a compound as set forth in Structure A, such as Compound II or III, thereby treating the subject.

In one embodiment, the invention provides a method of treating a subject having or at risk of having stroke comprising administering to the subject a therapeutically effective amount of a compound as set forth in Structure A, such as Compound II or III, thereby treating the subject.

In one embodiment, the invention provides a method of treating a subject having or at risk of having ARDS comprising administering to the subject a therapeutically effective amount of a compound as set forth in Structure A, such as Compound II or III, thereby treating the subject.

In one embodiment, the invention provides a method of treating a subject having or at risk of having burns comprising administering to the subject a therapeutically effective amount of a compound as set forth in Structure A, such as Compound II or III, thereby treating the subject.

In one embodiment, the invention provides a method of treating a subject having or at risk of having arthritis comprising administering to the subject a therapeutically effective amount of a compound as set forth in Structure A, such as Compound II or III, thereby treating the subject.

In one embodiment, the invention provides a method of treating a subject having or at risk of having edema comprising administering to the subject a therapeutically effective amount of a compound as set forth in Structure A, such as Compound II or III, thereby treating the subject.

In one embodiment, the invention provides a method of treating a subject having or at risk of having hypovolemic shock comprising administering to the subject a therapeutically effective amount of a compound as set forth in Structure A, such as Compound II or III, thereby treating the subject.

In one embodiment, the invention provides a method of treating a subject having or at risk of having hemorrhagic shock comprising administering to the subject a therapeutically effective amount of a compound as set forth in Structure A, such as Compound II or III, thereby treating the subject.

In one embodiment, the invention provides a method of treating a subject having or at risk of having chronic obstructive pulmonary disorder comprising administering to the subject a therapeutically effective amount of a compound as set forth in Structure A, such as Compound II or III, thereby treating the subject.

In one embodiment, the invention provides a method of treating a subject having or at risk of having asthma comprising administering to the subject a therapeutically effective amount of a compound as set forth in Structure A, such as Compound II or III, thereby treating the subject.

In one embodiment, the invention provides a method of treating a subject having or at risk of having acute or adult respiratory distress syndrome comprising administering to the subject a therapeutically effective amount of a compound as set forth in Structure A, such as Compound II or III, thereby treating the subject.

In one embodiment, the invention provides a method of treating a subject having or at risk of having vascular leakage syndrome (VLS) comprising administering to the subject a therapeutically effective amount of a compound as set forth in Structure A, such as Compound II or III, thereby treating the subject.

In one embodiment, the invention provides a method of treating a subject having or at risk of having retinopathy or vitreoretinal disease comprising administering to the subject a therapeutically effective amount of a compound as set forth in Structure A, such as Compound II or III, thereby treating the subject.

In one embodiment, the invention provides a method of treating a subject having or at risk of having age related macular degeneration comprising administering to the subject a therapeutically effective amount of a compound as set forth in Structure A, such as Compound II or III, thereby treating the subject.

In one embodiment, the invention provides a method of treating a subject having or at risk of having macular edema comprising administering to the subject a therapeutically effective amount of a compound as set forth in Structure A, such as Compound II or III, thereby treating the subject.

In one embodiment, the invention provides a method of treating a subject having or at risk of having uveitis comprising administering to the subject a therapeutically effective amount of a compound as set forth in Structure A, such as Compound II or III, thereby treating the subject.

In one embodiment, the invention provides a method of treating a subject having or at risk of having ischemic or reperfusion related tissue injury or damage, comprising administering to the subject a therapeutically effective amount of a compound as set forth in Structure A, such as Compound II or III, thereby treating the subject.

In one embodiment, the invention provides a method of treating a subject having or at risk of having autoimmune disease, comprising administering to the subject a therapeutically effective amount of a compound as set forth in Structure A, such as Compound II or III, thereby treating the subject.

In one embodiment, the invention provides a method of treating a subject having or at risk of having transplant rejection, comprising administering to the subject a therapeutically effective amount of a compound as set forth in Structure A, such as Compound II or III thereby treating the subject.

In one embodiment, the invention provides a method of treating a subject having or at risk of having inflammatory disease, comprising administering to the subject a therapeutically effective amount of a compound as set forth in Structure A, such as Compound II or III, thereby treating the subject.

In one embodiment, the invention provides a process for making a pharmaceutical composition comprising combining a combination of a compound set forth in Structure A, such as Compound II or III, in pharmaceutically acceptable N-oxides, salts, hydrates, solvates, crystal forms salts and individual diastereomers thereof and a pharmaceutically acceptable carrier.

In one embodiment, the invention provides a pharmaceutical composition comprising a compound as set forth in Structure A, such as Compound II or III, in a pharmaceutically acceptable carrier.

In one embodiment, the invention provides a method for inhibiting or reducing vascular leakage in a subject, comprising administering to a subject in need thereof an effective amount of IL-2 in combination with a compound of Structure A, such as Compound II or III, thereby reducing vascular leakage in the subject.

In one embodiment, the invention provides a pharmaceutical composition comprising IL-2 and at least one compound as set forth in Structure A, such as Compound II or III, in a concentration effective to reduce vascular leakage associated with IL-2 administration.

In one embodiment, the invention provides a method for treating cancer or a tumor in a subject, comprising administering to a subject in need thereof an effective amount of a therapeutic antibody, chemotherapeutic agent or immunotoxic agents, in combination with a compound set forth in Structure A, such as Compound II or III, thereby treating the cancer or tumor in the subject.

In one embodiment, the invention provides a pharmaceutical composition comprising a therapeutic agent and at least one compound as set forth in Structure A, such as Compound II or III, in a concentration effective to treat cancer in a subject. The cancer may be any cancer, including but not limited to an alimentary/gastrointestinal tract cancer, colon cancer, liver cancer, skin cancer, breast cancer, ovarian cancer, prostate cancer, lymphoma, leukemia, kidney cancer, lung cancer, muscle cancer, bone cancer, bladder cancer or brain cancer.

In one embodiment, the invention provides a method for treating a T-cell mediated disorder, comprising the administration of a therapeutically effective amount of at least one compound set forth in Structure A, such as Compound II or III, in a pharmaceutically acceptable N-oxide, salt, hydrate, solvate, crystal form salt and individual diastereomer thereof, to a subject in need of such treatment.

In one embodiment, the invention provides a method of treating acute myocardial infarction, comprising the administration of a therapeutically effective amount of an inhibitor of phosphoinositide-3-kinase. The inhibitor of phosphoinositide-3-kinase can be administered in combination with an anti-inflammatory agent, a therapeutic agent, a chemotherapeutic agent, an immunomodulatory agent, a therapeutic antibody, or a combination thereof.

In one embodiment, the invention provides a pharmaceutical composition, comprising 3-(2,4-diaminopteridine-6-yl) phenol (Compound II), or a pharmaceutically acceptable salt thereof, and a pharmaceutically acceptable carrier therefor.

In one embodiment, the invention provides a pharmaceutical composition, comprising 6-(1-H-indol-4-yl)pteridine-2,4-diamine (Compound III), or a pharmaceutically acceptable salt thereof, and a pharmaceutically acceptable carrier therefor.

DETAILED DESCRIPTION OF THE INVENTION

Figure 1:
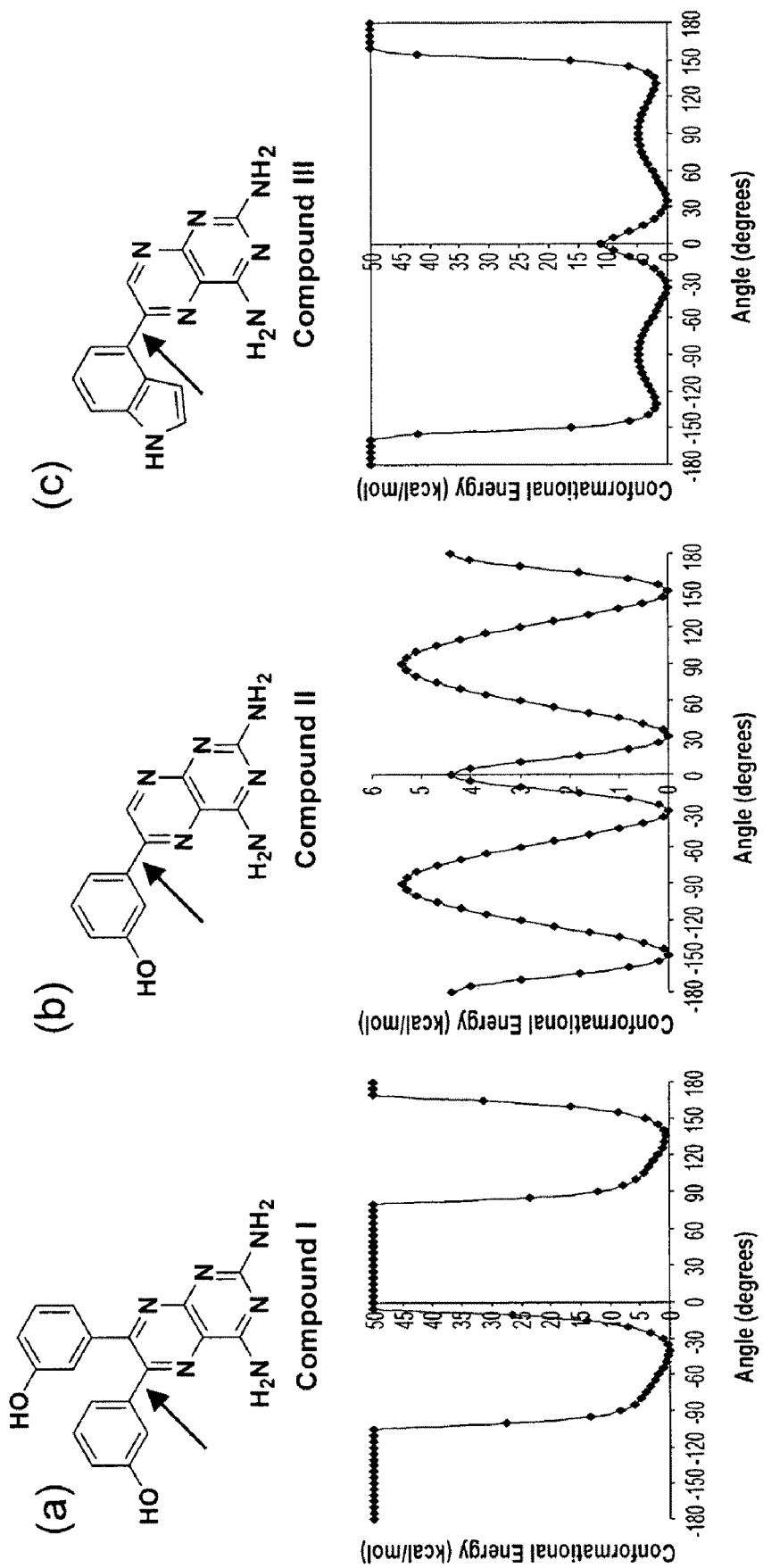
FIG. 1. Molecular models and conformational energy plots. (a-c) Structure diagrams and dihedral energy plots for Compounds I, II and III. Plots depict the barrier to rotation around the core pteridine and ring A; for Compound I, there are two rings (A to the left, B to the right). Arrows indicate the rotated bond.

The present invention is based on the discovery that certain chemical compounds are effective in inhibiting phosphoinositide 3-kinases, more specifically the PI3Kγ/δ isoforms. Such compounds are useful for treating adverse heart conditions, for example, by decreasing the magnitude of infarct damage to cardiac tissues following myocardial infarction and reperfusion. The invention provides compounds which are vasculostatic agents and methods of use thereof. Invention compounds are useful in treating a variety of disorders, including but not limited to myocardial infarction, stroke, cancer, vascular leakage syndrome (VLS), ocular and retinal disease, bone disease, pleural effusion, edema, inflammatory diseases, respiratory diseases, and ischemia. The term "vasculostasis" is hereby defined as referring to the maintenance of a homeostatic vascular functioning, and "vasculostatic agents" as agents that seek to address conditions in which vasculostasis is compromised by preventing the loss of or restoring or maintaining vasculostasis.

The present invention suggests that selectively inhibiting pro-inflammatory PI3K isoforms during the reperfusion phase prevents or inhibits overall tissue damage seen in ischemia/reperfusion injuries, such as myocardial infarction. Pan-reactive and isoform-restricted PI3K inhibitors were identified by screening a chemical family; molecular modeling studies attributed isoform specificity based on rotational freedom of substituent groups. Compound I, identified as a selective PI3K γ/δ inhibitor potently inhibited edema and inflammation in response to multiple mediators known to participate in myocardial infarction, including vascular endothelial growth factor and platelet activating factor; by contrast endothelial cell mitogenesis, a repair process important to tissue survival following ischemic damage, was not disrupted. In rigorous animal MI models, this compound provided potent cardioprotection, reducing infarct development and preserving myocardial function. Importantly, this was achieved when dosing well after myocardial reperfusion (up to 3 hours post), the same time period when patients are most accessible for therapeutic intervention. By targeting pathologic events occurring relatively late in myocardial damage, applicants have identified a potential means of addressing an elusive clinical goal: meaningful cardioprotection following delivery in the post-reperfusion time-period.

The PI3Kγ and δ isoforms in particular are promising targets, as genetic deletion studies establish their roles in edema and inflammatory responses. By contrast, PI3Kα and β two broadly expressed isoforms, apparently play more fundamental biologic roles as genetic deletion of either is lethal. Along with possible pitfalls from disrupting developmental events, anti-PI3K therapies are also complicated by the potential for pro-apoptotic activity. Considerable evidence supports a pro-survival role for PI3K (and its downstream target Akt) during ischemia, and although the exact isoform(s) involved remain unclear, in general PI3K pathways are considered beneficial events that should not be disrupted during I/R injuries. Additionally, while commonly employed PI3K inhibitors reduce inflammatory events in animal models, they have failed to reduce infarct size when delivered post-reperfusion. Finally, transgenic mice overexpressing a kinase-inactive PI3Kγ in their cardiomyocytes develop equivalent sized infarcts as do wild type animals following I/R injury.

As a step towards resolving this question, the present invention compounds have been shown to effectively inhibit PI3Kγ/δ to interrupt the reperfusion phase of I/R injury. Compound I was confirmed as a potent inhibitor of edema and inflammation induced by both RTK and GPCR ligands, but which at the same time spared tissue repair processes such as endothelial cell (EC) mitogenesis. In MI models designed to aggressive standards, it both reduced infarct development and improved myocardial function. Most impressively, cardioprotection was seen upon delivery up to several hours following reperfusion, a time when MI patients are available for therapeutic intervention in acute care settings, supporting the hope that this approach to selective PI3K isoform inhibition holds promise for bridging that gap between preclinical efficacy and clinical utility.

The data presented support the hypothesis that broadly blocking pro-inflammatory processes can limit I/R injury even well after the initiation of ischemic damage. To achieve this efficacy, a novel kinase inhibitor, Compound I, was utilized and selected for three specific properties. First, this compound inhibited PI3Kγ and to a lesser degree PI3Kδ with excellent specificity. Second, cell signaling events were blocked selectively rather than globally. Third, both endothelium and leukocyte-associated aspects of inflammation induced by multiple and diverse mediators were effectively antagonized. As final proof of these properties' value, the present invention proved cardioprotective when delivered well into the reperfusion period in both rodent and porcine models of acute MI.

Molecular modeling studies provided a basis for understanding PI3K isoform specificity based on the freedom of conformational rotation permitted by ring substituents, with rotational restrictions resulting in increased specificity. By inhibiting PI3Kγ and δ while sparing α and β isoforms, selective inhibition of inflammation-associated aspects of VEGF signaling was achieved. Of direct relevance to cardioprotection, PI3Kγ/δ inhibition blocked VEGF signaling events that trigger edema (VE cadherin phosphorylation) while sparing those that control mitogenesis (ERK phosphorylation). VEGF plays both positive (pro-angiogenic) and negative (pro-edema) roles in I/R injuries, with PI3K regulating both activities, therefore differentiating between these processes should be beneficial in any proposed MI therapy.

In similar manner as VEGF, PI3K also plays potentially conflicting roles in the response to I/R injury. The PI3K pathway is generally regarded as anti-apoptotic (or pro-cell survival), whereas genetic knock-out studies characterize PI3Kγ and δ as pro-inflammatory (or anti-tissue survival). The present findings suggest that this apparent dichotomy can be overcome by tailoring PI3K inhibition to specific isoforms and time periods. PI3K's pro-survival activity has best been demonstrated during the ischemic phase of MI development; as we only inhibited PI3K post-reperfusion, disrupting pro-survival signaling in ischemic cardiomyocytes was avoided. Additionally, while total PI3K blockade might be detrimental to tissue survival, the same is not necessarily true for isoform-specific intervention. For example, wortmannin eliminates the cardioprotective effects of numerous agents including insulin, IGF-I, erythropoietin, adrenomedullin and opioids, as well as both ischemic pre- and postconditioning, demonstrating the potential for at least some PI3K isoforms to ameliorate ischemic tissue damage. Transgenic mice overexpressing a kinase-inactive PI3Kγ in their cardiomyocytes, however, develop equivalent sized infarcts as do wild type mice, suggesting that this isoform at least is not requisite for balancing cardiomyocyte survival. Of course the fact that these transgenic mice do not show reduced infarcts is not germane to our argument that PI3Kγ/δ inhibition provides cardioprotection, as we propose that systemically administered Compound I has as its primary target of action leukocytes and vascular endothelium, not cardiomyocytes.

The anti-edema and anti-inflammatory activities observed upon PI3Kγ/δ inhibition was demonstrated when directed against either RTK or GPCR agonists (VEGF or histamine and PAF, respectively), supporting the concept that PI3K inhibition can achieve the broad ligand blocking profile required for effective reduction of reperfusion injury. Two mediators of particular interest were VEGF and PAF. Both are produced by ischemic myocardium and both act directly on EC to promote vascular permeability. VEGF-driven edema particularly has been implicated as a major factor underlying infarct progression. In addition to inducing edema, PAF also promotes leukocyte adherence to hypoxic endothelium, activates neutrophils and platelets, and is a negative inotrope (leading to cardiodepression via PI3Kγ signaling). The ability of Compound I to antagonize both VEGF and PAF-mediated inflammation was therefore a positive step in proposing these compounds as a cardioprotectant.

Rodent and porcine MI models confirmed these cardioprotective actions. A major goal was to provide weight to these data by designing studies to aggressive standards. Therefore, while ischemic phases <60 minute coupled with <6 hour endpoints are commonly employed, applicants adopted 60-90 minute ischemic periods and measured infarcts 24 hour post-initiation as recommended by an NIH-convened expert panel (see Bolli, R., Becker, L., Gross, G., Mentzer, R., Jr., Balshaw, D., & Lathrop, D. A. (2004) *Circ. Res.* 95, 125-134). Most importantly, all therapeutic interventions were administered post-reperfusion rather than during ischemia or even pre-ischemia as is routinely reported. Adopting these aggressive standards limited the achievable extent of infarct reduction, as considerable myocardial death would have occurred in the time between ischemia onset and therapeutic intervention. Despite this challenge, PI3Kγ/δ inhibition reduced infarct size by ~40% in both rodent and porcine-based studies. In the rat maximal efficacy was achieved when dosed with Compound I as late as 3 hour post-reperfusion (4 hours after the initial ischemic injury), and a single dosing on the day of infarction was sufficient to yield a durable functional benefit (improved fractional shortening 4 weeks later). This hopefully serves the goal of producing data better predictive of potential performance in the intended clinical environment, where patients are most likely to receive cardioprotective therapy post-diagnosis of an evolving MI if not post-reperfusion, after meaningful ischemic and even reperfusion injury has already occurred Te present invention demonstrates that PI3K inhibition represents a promising approach to limiting I/R injuries such as acute MI provided that the appropriate kinase inhibitor can be identified. Consensus is building that isoform specificity must be successfully addressed when developing PI3K inhibitors, with both δ and γ isoforms ranking high as potential targets. For example, an inhibitor slanted towards the γ isoform (but also inhibiting PI3Kα/β/δ at <300 nM) was recently shown to inhibit rheumatoid arthritis and lupus nephritis. The present data extend these concepts by demonstrating the value of PI3Kγ/δ inhibition in inflammatory-based but non-autoimmune pathologies. Applicants believe that the present invention meets several criteria that support its development as a cardioprotective therapy, in that it is specific against its targets, is deliverable by the clinically appropriate route (i.v.) during the clinically appropriate period (post-reperfusion), achieves relatively high efficacy at relatively low doses, and provides maximal efficacy within a relatively wide therapeutic window.

In one embodiment, exemplary compounds of structure (A) used in methods of the invention have the structure:

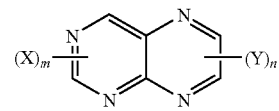

(A)

wherein:
each X is independently H, or $NH_2$
each Y is independently hydrogen, or

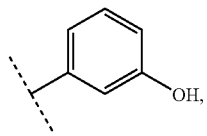

or other regio-isomeric phenols or

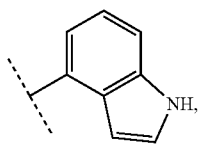

or other regio-isomeric indoles, or indazoles and m and n are each independently 1 or 2.

Exemplary compounds, as shown in Compounds II or III can be used as inhibitors of phosphoinositide-3-kinase.

Exemplary compounds of structure A include pteridines, such Compounds I, II, or III:

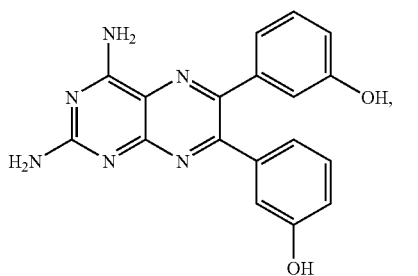

(I)

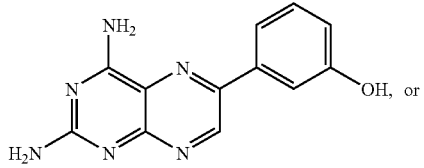

(II)

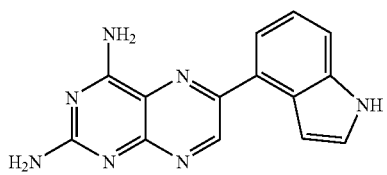

(III)

As used herein, the term "heterocyclic", when used to describe an aromatic ring, means that the aromatic ring contains at least one heteroatom. As used herein, the term "heteroatom" refers to N, O, S, and the like.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "lower alkyl" refers to alkyl groups having from 1 to about 6 carbon atoms.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl, wherein alkyl is as defined above, and "substituted alkoxy" refers to alkoxyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", when not used with reference to an aromatic ring, refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to carbon or heterocyclic groups in the ring further bearing one or more substituents as set forth above.

As used herein, "alkylaryl" refers to alkyl-substituted aryl groups and "substituted alkylaryl" refers to alkylaryl groups further bearing one or more substituents as set forth above.

As used herein, "arylalkyl" refers to aryl-substituted alkyl groups and "substituted arylalkyl" refers to arylalkyl groups further bearing one or more substituents as set forth above.

As used herein, "arylalkenyl" refers to aryl-substituted alkenyl groups and "substituted arylalkenyl" refers to arylalkenyl groups further bearing one or more substituents as set forth above.

As used herein, "arylalkynyl" refers to aryl-substituted alkynyl groups and "substituted arylalkynyl" refers to arylalkynyl groups further bearing one or more substituents as set forth above.

As used herein, divalent aromatic groups having in the range of 6 up to 14 carbon atoms and "substituted arylene" refers to arylene groups further bearing one or more substituents as set forth above.

As used herein, "oxyarylene" refers to the moiety "O-arylene", wherein arylene is as defined above and "substituted oxyarylene" refers to oxyarylene groups further bearing one or more substituents as set forth above.

Invention compounds can be prepared by a variety of methods well-known to those skilled in the art. Some such methods are illustrated in the "Examples" portion of the present application as shown below.

Pteridines contemplated for use in the methods of the present invention have the structure (A):

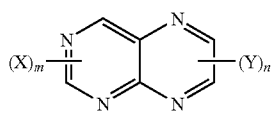
(A)

wherein:
each X is independently H, or $NH_2$
each Y is independently hydrogen, or

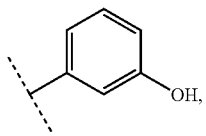

or other regio-isomeric phenols or

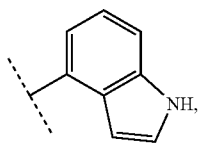

or other regio-isomeric indoles, or indazoles;
and
m and n are each independently 1 or 2.

In one embodiment, the present invention is based on the discovery that a combination therapy including interleukin-2 (IL-2) and chemical compounds described herein, some of which are effective kinase inhibitors, administered during IL-2 therapy, mitigates or lessens the adverse effects of IL-2. While not wanting to be bound by a particular theory, it is likely that the effect occurs while preserving or enhancing the beneficial effect of IL-2 such that the disease or disorder is treated. While IL-2 is described in the present application as an illustrative example, it should be understood that the invention includes combination therapy including a compound of the invention, including but not limited to vasculostatic agents, such as lipid, tyrosine, serine or threonine kinase inhibitors, for example, Src-family inhibitors, immunomodulatory molecules and phosphoinositide kinases. In particular, such immunomodulatory molecules include those that result in vascular leakage. Cytokines, and in particular IL-2, are examples of such immunomodulatory molecules.

Such inhibitors, in combination with IL-2, are effective in blocking vascular leakage typically associated with IL-2 administration. Thus, compositions and methods are provided for treating disorders associated with VLS. In one embodiment, the invention provides a composition containing a therapeutically effective amount of IL-2 and a vasculostatic agent or compound as described herein in a pharmaceutically acceptable carrier.

Some of the compounds are kinase inhibitors, such as phosphoinositide kinases, and therefore are useful in treating a wide variety of disorders resulting from aberrant kinase activity, in addition to treating disorders associates with IL-2 administration. Kinase-associated disorders are those disorders which result from aberrant kinase activity, and/or which are alleviated by the inhibition of one or more enzymes within a kinase family. For example, Lck inhibitors are of value in the treatment of a number of such disorders (e.g., the treatment of autoimmune diseases), as Lck inhibition blocks T cell activation. Similarly, Src family inhibitors are of value in treating a variety of cancers as Src inhibition impacts tumor cell invasion, metastases and survival.

The compounds and methods of the present invention, either when administered alone or in combination with other agents described herein (e.g., chemotherapeutic agents or protein therapeutic agents) are useful in treating a variety of disorders including but not limited to, for example: stroke, cardiovascular disease, chronic obstructive pulmonary disorder, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), cancer, pleural effusions, rheumatoid arthritis, diabetic retinopathy, uveitis, macular edema, retinitis pigmentosa, and retinopathies, including diabetic retinopathy and retinopathy of prematurity, inflammatory diseases, restenosis, edema (including edema associated with pathologic situations such as cancers and edema induced by medical interventions such as chemotherapy), asthma, acute or adult respiratory distress syndrome (ARDS), lupus, vascular leakage, transplant (such as organ transplant, acute transplant or heterograft or homograft (such as is employed in burn treatment)) rejection; protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; cancers, including those where kinases such as PI-kinases pathways are implicated directly or indirectly, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemia/reperfusion injury); dermatomyositis; alopecia greata; chronic actinic dermatitis; eczema; Behcet's disease; Pustulosis palmplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; von Hippel Lindau disease; and the like.

"Treating cancer" as used herein refers to providing a therapeutic benefit to the cancer patient, e.g. the therapy extends the mean survival time of patients, increases the percentage of patients surviving at a given timepoint, extends the mean time to disease progression, reduces or stabilizes tumor burden or improves quality of life for the patient or any of the above, for example. While not wanting to be bound by a particular theory, some of the compounds of the invention may be cytostatic and therefore have activity directly on the tumor cells.

"Shock" as used herein refers to fluid loss arising from either hypovolemic or hemorrhagic shock, for example blood loss arising from acute penetrating trauma, severe gastrointestinal bleeding disorders and rapid secondary fluid loss arising from medical or surgical conditions due to inadequate circulating volume followed by subsequent inadequate perfusion.

"Hypovolemic shock" as used herein refers to a medical or surgical condition in which rapid fluid loss results in multiple organ failure due to inadequate circulating volume and subsequent inadequate perfusion."

"Hemorrhagic shock" as used herein refers to acute external blood loss arising, for example, blood loss from acute penetrating trauma, severe GI bleeding disorders and acute internal blood loss into the thoracic and abdominal cavities.

"Chronic obstructive pulmonary disorder" as used herein refers to a slowly progressive disorder characterized by airflow obstruction often arising from an inflammatory response and may also be referred to clinically as, emphysema, chronic obstruction, non-reversible obstructive airways disease chronic obstructive airways disease and chronic obstructive lung disease.

As used herein, "kinase" refers to any enzyme that catalyzes the addition of phosphate groups to a protein or lipid residue, for example, serine, threonine and various classes and sub-classes of phosphoinositide kinases catalyze the addition of phosphate groups to serine, threonine and various classes and sub-classes of inositol, or lipid or protein or peptide residues.

As used herein, the terms "PI3K," "PI3 kinase," "PI3 kinases," "PI3 kinase family," or "PI3K family" refer to related homologs or analogs belonging to the mammalian family of phosphoinositide-3 kinases.

Uninhibited PI3K family of enzymes can mediate injurious events in conditions such as ischemia, ischemia/reperfusion injury, and inflammatory situations such as VEGF-driven edema and PMN infiltration; therefore, inhibiting PI3Ks can be used for achieving important medical objectives, for example, in course of treatment of a patient following myocardial ischemia to reduce infarct development.

The present invention also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the present invention. Thus, in one aspect, the invention provides a pharmaceutical composition including both a therapeutic and a compound of the invention wherein the compound is present in a concentration effective to reduce vascular leakage associated with indications or therapeutics which have vascular leak as a side-effect.

For example, administration of a compound of the invention in conjunction with IL-2, immunotoxins, antibodies or chemotherapeutics. In these cases, IL-2, immunotoxin, antibody or chemotherapeutic concentration can be determined by one of skill in the art according to standard treatment regimen or as determined by an in vivo animal assay, for example.

The present invention also provides pharmaceutical compositions comprising IL-2, immunotoxin, antibody or chemotherapeutic and at least one invention compound in an amount effective for inhibiting vascular permeability, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the invention compounds are included in the present invention.

Invention pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or pharmaceutical composition to the subject in need of treatment.

The pharmaceutical compositions for the administration of the compounds of this embodiment either alone or in combination with IL-2, immunotoxin, antibody or chemotherapeutic may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether β-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one aspect, the invention compounds are administered in combination with an anti-inflammatory, antihistamines, chemotherapeutic agent, immunomodulator, therapeutic antibody or a kinase inhibitor, e.g., a tyrosine or a serine/threonine, or a lipid kinase inhibitor or PI3 kinase family members, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-demethoxydaunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 1) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

The term antibody as used in this invention is meant to include intact molecules of polyclonal or monoclonal antibodies, as well as fragments thereof, such as Fab and F(ab')$_2$, Fv and SCA fragments which are capable of binding an epitopic determinant.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which involve compromised vasculostasis an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was preferred at 0.1 mg/kg/day while another was effective at about 1.0 mg/kg/day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. There may be a period of no administration followed by another regimen of administration. Preferably, administration of the compound is closely associated with the schedule of IL-2 administration. For example, administration can be prior to, simultaneously with or immediately following IL-2 administration It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Another embodiment described herein is based on the discovery that a compound that is a vasculostatic agent alone or in combination with an effective amount of therapeutic antibody (or therapeutic fragment thereof), chemotherapeutic or immunotoxic agent, is an effective therapeutic regimen for treatment of tumors, for example. While doxorubicin, docetaxel, or taxol are described in the present application as illustrative examples of chemotherapeutic agents, it should be understood that the invention includes combination therapy including a compound of the invention, including but not limited to vasculostatic agents, such as tyrosine, serine or threonine kinase inhibitors, for example, lipid kinases, or PI3-kinases, and any chemotherapeutic agent or therapeutic antibody.

Such vasculostatic agents, in combination with chemotherapeutic agents or therapeutic antibodies are effective in blocking vascular permeability and/or vascular leakage and/or angiogenesis. In one embodiment, the invention provides a composition containing a therapeutically effective amount of a chemotherapeutic agent and a vasculostatic agent in a pharmaceutically acceptable carrier.

In one embodiment, the invention provides a method for reducing the tumor burden in a subject, comprising administering to a subject in need thereof an effective amount of chemotherapeutic agent in combination with a compound that is a vasculostatic agent. In an illustrative example, the method includes use of at least one of the invention compounds e.g., as set forth in Structure A or any combination thereof, with the chemotherapeutic agent. It should be understood that the tumor burden in a subject can be reduced prior to treatment with a compound of the invention through surgical resection, chemotherapy, radiation treatment or other methods known to those of skill in the art.

The compounds according to this invention may contain one or more asymmetric carbon atoms and thus occur as racemates and racemic mixtures, single enantiomers, diastereomeric mixtures and individual diastereomers. The term "stereoisomer" refers to a chemical compounds which differ from each other only in the way that the different groups in the molecules are oriented in space. Stereoisomers have the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. All such isomeric forms of these compounds are included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. The terms "optically pure compound" or "optically pure isomer" refers to a single stereoisomer of a chiral compound regardless of the configuration of the compound.

Several illustrative compounds employed in the methods of the present invention are inhibitors of kinases and therefore are useful in treating a wide variety of disorders resulting from aberrant kinase activity. Some examples of kinases that can be inhibited by compounds of the present invention include PI-kinases and their associated disorders, which result from aberrant lipid kinase activity, and/or which are alleviated by the inhibition of one or more of the enzymes within the PI kinases. For example, PI-Kinase inhibitors are of value in the treatment of cancer, as PI-Kinase inhibition blocks tumor cell migration and survival. Many compounds of the invention are also broad spectrum kinase inhibitors and inhibit other kinases in addition to PI-kinases kinases or lipid kinases.

Another example of a kinase that can be inhibited by compounds of the present invention include phosphoinositide-3 kinases (PI3K) and their associated disorders. Compounds capable of serving as PI3K inhibitors include derivatives of pteridine having the general structure (A) or a pharmaceutically acceptable salt, hydrate, solvate, crystal form or individual diastereomers thereof, where X, Y, m and n are as described above:

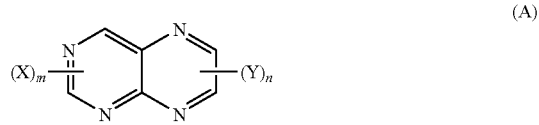

(A)

One example of a specific compound that can be employed as a PI3K inhibitor is 6,7-bis-(3-hydroxyphenyl)-pteridine-2,4-diamine having the formula I (Compound I), or a pharmaceutically acceptable salt, hydrate, solvate, crystal form, N-oxide or individual diastereomer thereof:

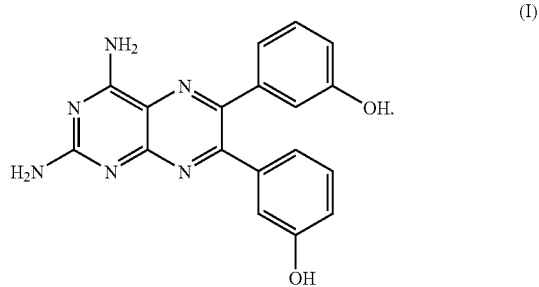

(I)

Another example of a specific compound that can be employed as a PI3K inhibitor is 3-(2,4-diaminopteridin-6-yl)phenol having the formula II (Compound II), or a pharmaceutically acceptable salt, hydrate, solvate, crystal form, N-oxide or individual diastereomer thereof:

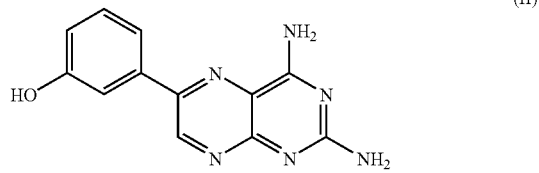

(II)

Another example of a specific compound that can be employed as a PI3K inhibitor is 6-(1H-Indol-4-yl)pteridine-2,4-diamine having the formula III (Compound III), or a pharmaceutically acceptable salt, hydrate, solvate, crystal form, N-oxide, or individual diastereomer thereof:

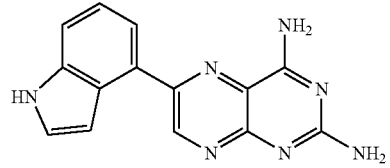

(III)

Compound (I), a specific PI3K inhibitor, was developed and initially identified based on its ability to inhibit edema formation in VEGF-treated animals; PI3K inhibition was confirmed by the blockade of Akt phosphorylation following VEGF delivery (Akt being a direct PI3K target).

Cancers that may be treated by compounds of the invention alone or as a combination therapy of the invention include but are not limited to a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, a muscle cancer, a bone cancer, bladder cancer or a brain cancer.

The present invention also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the present invention. Thus, in one aspect, the invention provides a pharmaceutical composition including both a chemotherapeutic agent, immunotoxin or therapeutic antibody and a compound of the invention wherein the compound is present in a concentration effective to reduce tumor burden, for example. In one aspect, the invention provides a pharmaceutical composition including a compound of the invention, wherein the compound is present in a concentration effective to reduce vascular permeability, for example. The concentration can be determined by one of skill in the art according to standard treatment regimen or as determined by an in vivo animal assay, for example.

Pharmaceutical compositions employed as a component of invention articles of manufacture can be used in the form of a solid, a solution, an emulsion, a dispersion, a micelle, a liposome, and the like, wherein the resulting composition contains one or more of the compounds described above as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The present invention also provides pharmaceutical compositions including at least one invention compound in an amount effective for treating a tumor, or cancer, alone or in combination with a chemotherapeutic agent, immunotoxin, immunomodulator or therapeutic antibody and a pharmaceutically acceptable vehicle or diluent. Similarly, the present invention provides pharmaceutical compositions including at least one invention compound capable of treating a disorder associated with vasculostasis in an amount effective therefore. Non-limiting examples of pharmaceutical compositions that can be used can include Compound I and a compound having cyclodextrin moiety, such as β-cyclodextrin, for example, sulfobutyl ether β-cyclodextrin. The molar ratio between Compound I and a cyclodextrin compound can be between about 0.2 and 5, for example, between about 0.5 and 4, such as between about 0.7 and 3.6.

The compositions of the present invention may contain other therapeutic agents as described herein and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The terms "administration of" and or "administering a" compound should be understood to mean providing a compound of the invention or pharmaceutical composition to the subject in need of treatment. For example, administration of the vasculostatic agent can be prior to, simultaneously with, or after administration of an invention compound or other agent. In the Examples provided herein, typically the compounds of the invention are co-administered at the same time as a chemotherapeutic agent.

While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, mechlorethamine. colchicine, demecolcine, etoposide, taxane, anthracycline antibiotic, doxorubicin, daunorubicin, caminomycin, epirubicin, idarubicin, mitoxanthrone, 4-demethoxy-daunomycin, 11-deoxydaunorubicin, 13-deoxydaunorubicin, adriamycin-14-benzoate, adriamycin-14-octanoate or adriamycin-14-naphthaleneacetate.

Compounds, their prodrugs, or metabolites employed in the methods of the present invention are vasculostatic agents such as inhibitors of vascular permeability and/or vascular leakage and/or angiogenesis. In addition, several illustrative compounds employed in the methods of the present invention are inhibitors of kinases and therefore are useful in treating a wide variety of disorders resulting from aberrant kinase activity. Kinase-associated disorders are those disorders which result from aberrant kinase activity, and/or which are alleviated by the inhibition of one or more of the kinases.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The Examples set out below include representative examples of aspects of the present invention. The Examples are not meant to limit the scope of the invention but rather serve exemplary purposes. In addition, various aspects of the invention can be summarized by the following description.

However, this description is not meant to limit the scope of the invention but rather to highlight various aspects of the invention. One having ordinary skill in the art can readily appreciate additional aspects and embodiments of the invention.

Example 1

Syntheses of Compounds Described

General Analytical Methods

All solvents are used without further purification. Reactions are usually run without an inert gas atmosphere unless specified otherwise. All $^1$H NMR are run on a 500 MHz Bruker NMR. Chemical shifts are reported in delta (δ) units, parts per million (ppm) downfield from tetramethylsilane. Coupling constants are reported in hertz (Hz). A Waters LC/MS system is used in identity and purity analysis. This system includes a 2795 separation module, a 996 photodiode array detector and a ZQ2000 mass spectrometer. A Zorbax SB column (150×4.6 mm 3.5μ, Agilent Technologies) is used for the LC. Column temperature is 40° C. Compounds are separated using gradient elution with mobile phases of water (0.05% TFA (A)) and acetonitrile (0.05% TFA (B)). Flow rate is 1 mL/min. The gradient program used in separation is 0-15 min: 5-60% B; 15-15.5 min: 60-100% B; 15.5-17 min: 100% B.

6,7-disubstituted pteridines; Method A

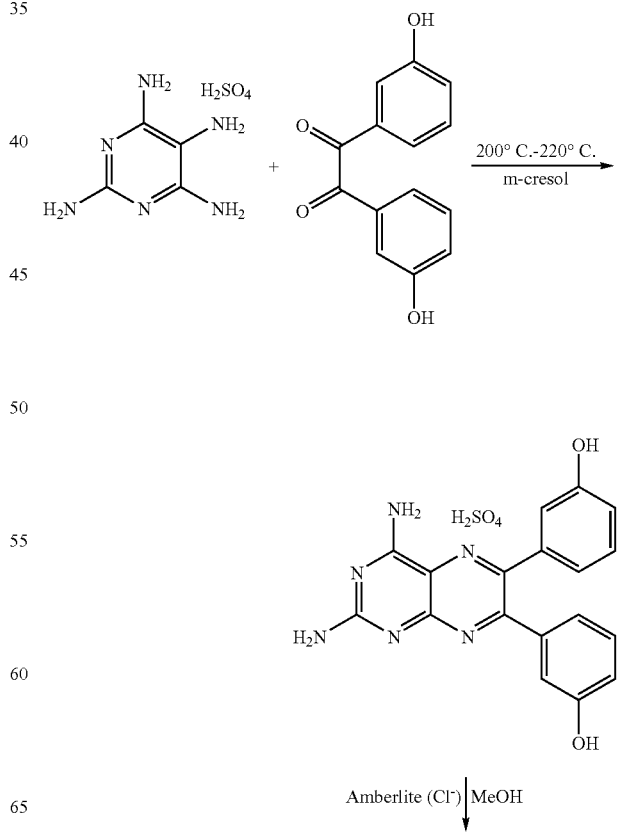

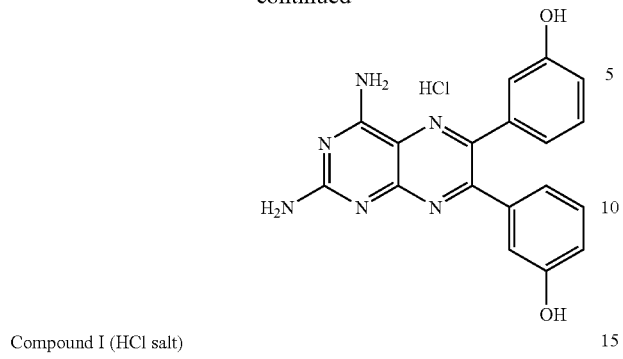

Compound I (HCl salt)

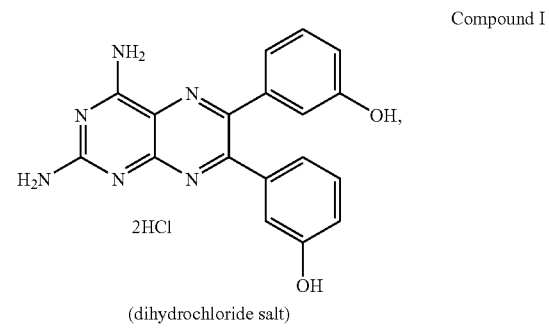

(dihydrochloride salt)

Method B

The pyrimidine is made into the free base with sodium carbonate, sodium bicarbonate or sodium hydroxide using solid or solution by using the appropriate number in equivalents to neutralize the acid or by adjusting the pH to neutral to slightly basic (ca. 7-9). The benzil or glyoxal is added and the solution is heated for 1 h-5 h. The free base formed precipitates out of solution and is washed successively with water, methanol and then ether. The solid is dried in vacuo.

Compound I

A 5-mL reaction vial with a stirring vane and a teflon cap was charged with 3,3'-dihydroxybenzil (Midori Kagaku Co Ltd; 121 mg; 0.500 mmol) and 0.700 mL of m-cresol (Acros) which gives a dull-yellow solution on warming to ca. 50° C. The clear solution is treated with 2,4,5,6-tetraminopyrimidine sulfate (Aldrich; 119 mg; 0.500 mmol; 1.00 equiv) which is insoluble in the reaction solution at room temperature and goes into solution on heating to ca. 200° C. to give an almost completely homogeneous dark greenish solution in about 30 min-45 min. Heating between 200° C. and 220° C. for an additional 1.5 h, followed by cooling to room temperature, and precipitation by pouring into 40 mL of anhydrous diethyl ether resulted in a greenish-yellow precipitate. The solid was centrifuged, the supernatant decanted, the solid precipitate washed with 5×40 mL of diethyl ether and dried in a vacuum dessicator to yield 0.275 g (124%) of a yellow-green solid. The additional mass is the reaction solvent, m-cresol. MS (M+H$^+$: calcd 347; found 347).

In case purified Compound I is required, the crude 3-[2,4-diamino-6-(3-hydroxyphenyl)pteridin-7-yl]phenol may be dissolved in methanol, and an aqueous solution of 2.0 equiv.-2.2 equiv. of sodium bicarbonate (or excess sodium bicarbonate) may be added to neutralize the acid making sure the pH is between 6 and 8 to ensure free-base. The free-base precipitates out of the methanol-water mixture within a few seconds. In case, precipitation does not occur, excess methanol ensures precipitation. The yellowish solid may be isolated and washed with acetonitrile-water or isopropanol-water mixtures and then with methanol-ether, and then ether (×3). The product is dried to yield the free base, Compound I.

In case the purified sulfate is required, the free base is protonated in MeOH by adding a conc. aqueous sulfuric acid (1.0 equiv) to a slurry of the compound in MeOH. The homogeneous protonated product is precipitated out by adding ether to the methanol.

A 125-mL amber-bottle with a stirring bar and a septum was charged with crude 6,7-bis(3-hydroxyphenyl)-pteridine-2,4-diamine (135 mg; 0.304 mmol) and 5 mL of methanol. To the resulting dark brownish-green solution was added Amberlite (Cl$^-$) resin (GFS Chemical; 5.20 g). The heterogeneous mixture was stirred gently for ca. 16 h. with an apparent visual lightening of the solution. The solution was filtered to remove the resin beads, which were rinsed with 5×8 mL of MeOH. The light brown solution was concentrated on a rotary evaporator to yield 133 mg of dark brown oil. The oil was redissolved in ca. 2 mL of MeOH, and added to 40 mL of diethyl ether to yield a flocculent yellow precipitate that was isolated by centrifuging and decanting the supernatant. The solid washed with 4×40 mL of diethyl ether, and dried in a vacuum dessicator to yield a greenish-yellow product (94.0 mg; 0.246 mmol; 81% for two steps). 98% purity by LC/MS (230 DAD). Mass-spec [ES$^+$]=347.7. $^1$H NMR (DMSO-d6) 6.78-6.87 (4H, m), 6.92-6.95 (2H, m), 7.12-7.16 (2H, m), 7.82 (1H, br.s), 8.68 (1H, br.s), 9.15 (1H, s), 9.25 (1H, s), 9.58 (1H, s), 9.72 (1H, s). C, N analysis: $C_{18}H_{16}C_{12}N_6O_2$ (Calcd.: C, 51.56; N, 20.04. Found: C, 51.64; N, 19.93).

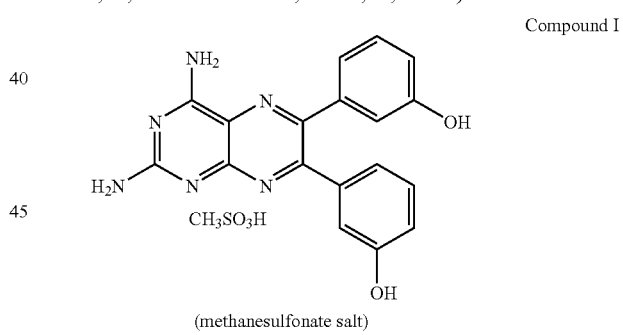

(methanesulfonate salt)

2.66 g (7.68 mmol) of Compound I was added to a solution of 1.55 g (16.13 mmol) of methanesulfonic acid in 20 mL of MeOH with stirring. Pteridine immediately dissolved to give a dark-greenish solution. The reaction mixture was stirred for 30 min and then added dropwise to 400 mL of diethyl ether with vigorous stirring. The formed yellow precipitate was collected, washed repeatedly with ether and dried in vacuo to give 3.36 g (99.1% yield) of the product as a light-yellow powder. 95.5% purity by LC/MS (230 DAD). Mass-spec [ES+]=347. $^1$H NMR (MeOH-d4) 2.71 (3H, s), 6.80-6.85 (2H, m), 6.90-6.92 (2H, m), 6.95 (1H, m), 7.00 (1H, m), 7.12-7.16 (2H, m).

Respiratory Distress Syndrome (ARDS) is an acute, severe injury to most or all of both lungs causing fluid leak into the lungs. Patients with ARDS experience severe shortness of breath and often require mechanical ventilation (life support)

because of respiratory failure. ARDS has also been called some of the following terms: Non-cardiogenic pulmonary edema; Increased-permeability pulmonary edema; Stiff lung; Shock lung; Adult respiratory distress syndrome; Acute respiratory distress syndrome. Two representative compounds of the invention were selected for initial study in the reduction of ARDS. NIH Swiss mice were given an intraperitoneal injection of 1.5 mg/kg Oleic Acid of (in this example formulated in saline) and/or invention compounds. Four hours subsequent to injection animals were sacrificed followed by collection, blotting and weighing (wet weight) of the lungs. Lungs were then dried at 80° C. for 24 hours and weighed (dry weight). N=4/group, Compound I, sulfate salt (compound E—in the 0.5 mg/kg range, in this example formulated in 50% PEG400: 50% water) typically reduced ARDS-induced edema by >50% while 4-[4-amino-6-(3,4-dihydroxyphenyl)pteridin-7-yl]benzene-1,2-diol (compound F—in the 0.5 mg/kg range, in this example formulated in 50% PEG400:50% water) typically reduced ARDS-induced edema by >100%. The results are shown in FIG. 12.

Example 2

Synthesis of 3-Aminopyrazine-2-carboxamide (Intermediate 1)

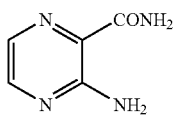

1

A solution of 3-amino-pyrazine-2-carboxylic acid methyl ester (5.0 g, 33 mmol) in concentrated ammonium hydroxide solution (30 mL) was heated at 60° C. for 3 h. The mixture was cooled to RT and the resulting solid filtered. After thoroughly washed with water followed by ether, the title compound was obtained as a brown solid (3.7 g, 82%).

$^1$H NMR (500 MHz, DMSO-$d_6$): δ 8.19 (d, J=2.4 Hz, 1H), 8.07 (br s, 2H), 7.80 (d, J=2.4 Hz, 1H), 7.59 (br s, 2H). MS (ES+): m/z 139 (M+H)$^+$.

Example 3

Synthesis of 3-Aminopyrazine-2-carbonitrile (Intermediate 2)

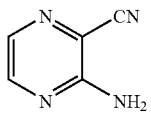

2

To a solution of intermediate 1 (3.5 g, 25 mmol) in DMF (40 mL) at RT was added POCl$_3$ (4.5 mL, 49 mmol) slowly. The resulting mixture was heated at 80° C. for 15 min and then cooled to RT. The mixture was poured into ice water and the mixture neutralized with 10% NaOH solution. The resulting solid was filtered and redissolved in 5% HCl. The solution was heated at 70° C. for 30 min and the resulting solid filtered. After thoroughly washed with water, the title compound was obtained as a brown solid (1.7 g, 56%). $^1$H NMR (500 MHz, DMSO-$d_6$): δ 8.28 (d, J=2.4 Hz, 1H), 7.90 (d, J=2.4 Hz, 1H), 7.32 (br s, 2H). MS (ES+): m/z 121 (M+H)$^+$.

Example 4

Synthesis of 3-Amino-6-bromopyrazine-2-carbonitrile (Intermediate 3)

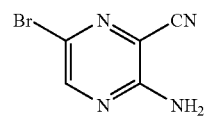

3

To a solution of intermediate 2 (1.7 g, 14 mmol) in acetic acid (40 mL) at RT was added bromine (0.95 mL, 19 mmol) slowly. The resulting mixture was heated at 60° C. for 30 min and then cooled to RT. The mixture was poured into ice water and the resulting solid filtered. After thoroughly washed with water, the title compound was obtained as a yellow solid (2.3 g, 83%). $^1$H NMR (500 MHz, DMSO-$d_6$): δ 8.44 (s, 1H), 7.60 (br s, 2H). MS (ES+): m/z 199 (M+H)$^+$.

Example 5

Synthesis of 6-Bromopteridine-2,4-diamine (Intermediate 4)

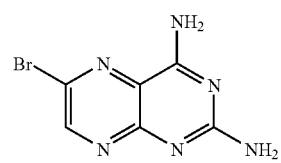

4

To a solution of guanidine hydrochloride (4.5 g, 47 mmol) in MeOH (50 mL) was added sodium methoxide (25 wt % in MeOH; 8.0 g, 37 mmol). After heating the mixture at reflux for 30 min, intermediate 3 (2.0 g, 10 mmol) was added and the mixture heated at reflux for additional 1 h. The reaction mixture was cooled to RT and then diluted with water until solid precipitated. After filtration and thoroughly washed with water followed by ether, the title compound was obtained as a light green solid (2.0 g, 83%). $^1$H NMR (500 MHz, DMSO-$d_6$): δ 8.77 (s, 1H), 7.72 (br s, 2H), 6.80 (br s, 2H). MS (ES+): m/z 241/243 (M+H)$^+$.

Example 6

Synthesis of 3-(2,4-diaminopteridin-6-yl)phenol (Compound II)

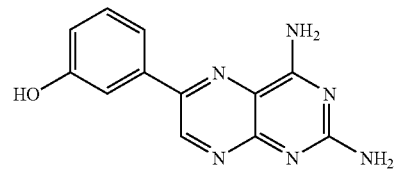

II

3-Hydroxyphenylglyoxal (2.10 g, 12.5 mmol) was dissolved in 100 mL of DI water. Acetone oxime (0.912 g, 12.5 mmol) was added, followed by 3 drops of 1N aqueous hydrochloric acid to bring the pH to ca. 2-3. This solution was stirred at 50° C. for one hour, then 2,4,5,6-tetraminopyrimidine sulfate (2.67 g, 11.2 mmol) was added and the reaction mixture was stirred at ambient temperature for 3 hours, then brought to reflux and refluxed for 6 hours. At this point it formed a thick yellow suspension. The reaction was allowed to cool down to ambient temperature. Saturated aqueous sodium bicarbonate was added dropwise to bring the pH to ca. 6-7. The precipitate was collected, washed extensively with water, then with 60 mL of methanol and repeatedly with diethyl ether and dried in vacuo to give 2.75 g of the title compound (96.5% yield) as a light-yellow solid.

m.p.: >300° C. $R_F$=0.31 ($CH_2Cl_2$:MeOH, 9:1 v/v). $^1H$ NMR (500 MHz, DMSO-$d_6$): δ 9.64 (s, 1H), 9.29 (s, 1H), 8.28 (br s, 1H), 8.21 (br s, 1H), 7.73 (d, J=8.0 Hz, 1H), 7.67 (t, J=1.9 Hz, 1H), 7.31 (t, J=7.9 Hz, 1H), 7.17 (br s, 2H), 6.89 (dd, J=7.9 Hz, J=2.3 Hz, 1H). $^{13}C$-NMR (125 Hz, DMSO-$d_6$): δ 163.0, 160.6, 157.9, 151.9, 147.5, 145.1, 136.8, 129.8, 121.6, 117.3, 116.5, 113.3. MS (ES+): m/z 255 (M+H)$^+$.

Example 7

Synthesis of 6-(1H-Indol-4-yl)pteridine-2,4-diamine (Compound III)

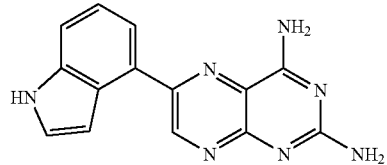

A suspension of intermediate 4 (0.20 g, 0.83 mmol), 1H-indol-4-yl-4-boronic acid (0.19 g, 1.2 mmol), Pd(PPh$_3$)$_4$ (90 mg, 0.078 mmol) and Na$_2$CO$_3$ solution (2 M; 1.0 mL, 2.0 mmol) in DMF (6 mL) was sealed in a microwave reaction tube and irradiated with microwave at 150° C. for 20 min. After cooling down to RT, the cap was removed and the resulting mixture filtered and the filtered solid washed with DCM. The filtrate was concentrated and the residue purified by column chromatography (DCM to 20% MeOH/DCM). The fractions were combined and the solvent removed. The residue was triturated in DCM and the title compound obtained as a light brown solid (0.12 g, 52%) after filtration.

m.p.: >300° C. $R_F$=0.36 ($CH_2Cl_2$:MeOH, 9:1 v/v). $^1H$ NMR (500 MHz, DMSO-$d_6$): δ 11.35 (s, 1H), 9.27 (s, 1H), 7.75 (br s, 1H), 7.70 (dd, J=7.4 Hz, J=0.8 Hz, 1H), 7.52 (d, J=8.0 Hz, 1H), 7.49 (t, J=2.8 Hz, 1H), 7.44 (br s, 1H), 7.24 (t, J=7.8 Hz, 1H), 6.99 (t, J=2.2 Hz, 1H), 6.70 (br s, 2H). $^{13}C$ NMR (125 Hz, DMSO-$d_6$): δ 163.1, 162.7, 154.4, 149.5, 146.2, 136.7, 127.9, 126.6, 125.1, 121.6, 121.1, 119.2, 112.6, 101.2. MS (ES+): m/z 278 (M+H)$^+$.

Example 8

Identification of PI3K isoform-selective inhibitors. Screening a novel family of pteridines for activity against class IA (α, β and δ) and IB (γ) PI3K isoforms identified pan-isoform inhibitors as well as more selective compounds which spares PI3Kα; FIG. 1 & Table 1. Compound I was demonstrated to inhibit PI3Kγ and δ (IC$_{50}$ values of 83 and 235 nM, respectively) while both PI3Kα and β were relatively unaffected (IC$_{50}$ values >1 uM).

Modeling studies indicated that the freedom of conformational rotation permitted by ring substituents governs isoform selectivity (FIG. 1). Generally, invention compounds allow for substituent ring energy minima at 30-40 degrees however each compound pays differing penalties as angles diverge from this range. Compound I exhibited the greatest barrier to rotation (most conformations >>50 kcal) and consequentially was highly isoform selective. Compound III demonstrating a high degree of conformational flexibility (ring A being almost freely rotatable with maxima ~5 kcal) was found to be less selective. Compound II occupies an intermediate position (several conformations <10 but some >>50 kcal).

Figure 2:
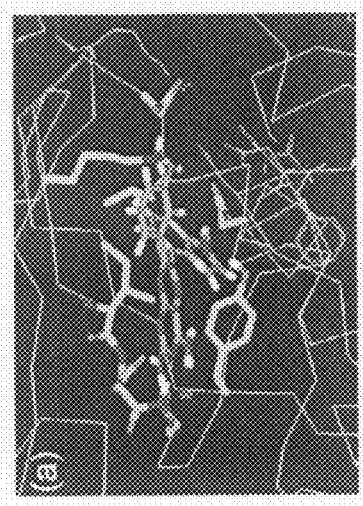
FIG. 2. Models of PI3K isoform-kinase inhibitor interactions. (a) Superposition of Compounds I, II and III in PI3Kγ showing preferred rotatable angles between ring A and the pteridine core. (b) Superposition of the same three compounds in PI3Kα. (c) Model structure of human PI3Kγ kinase (ribbon) with Compound I located in the catalytic domain.
Figure 2:
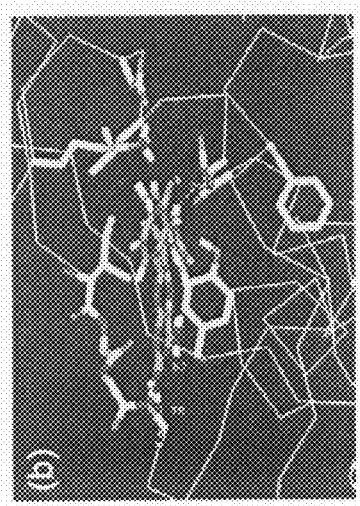
Figure 2:
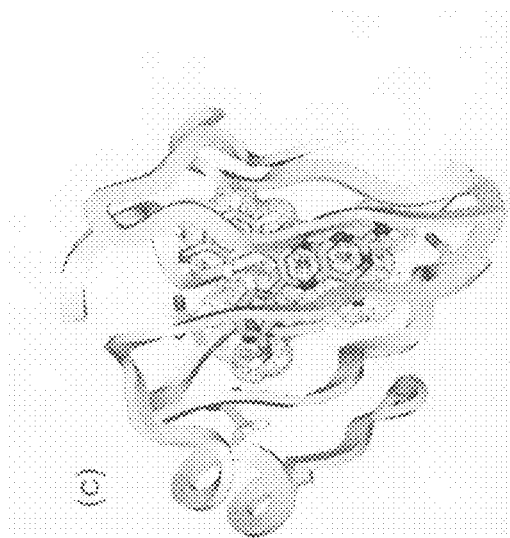

Regarding kinase isoforms, PI3Kγ is most tolerant of ring conformational variations followed by PI3Kδ, supporting a model in which these two kinases are more readily fit by all invention compounds; PI3Kα and β being less tolerant lock-out Compound I and partially Compound II (FIG. 2). For Compound I, modeling supports that two strong hydrogen bonds can form with the PI3Kγ hinge region: the N-3 nitrogen of the pteridine ring serving as an acceptor to the backbone NH of Val882 and the 2-primary amine group serving as donor to the same residue's backbone carbonyl. Additionally this compound and its 4-amino group is positioned adjacent to the backbone carbonyl of Glu880, however bond formation geometry is poor. These hydrogen bond patterns are similar to those for ATP as seen in the published ATP/PI3Kγ complex 1E8X, supporting a model for Compound I binding within the catalytic domain (FIG. 2c). Interactions are also formed outside the ATP binding site, where a pocket accommodates Compound I containing a 6' substituted meta-phenol and Asp841 (on the ka3 helix at the pocket's rear) forms a hydrogen bond with the OH group.

To place these data in context, two reagents commonly used as PI3K inhibitors were also profiled (Table 1). LY294002 was revealed as a relatively weak inhibitor (IC$_{50}$ values against PI3Kδ and β of 561 and 858 nM, respectively, and no meaningful activity against PI3K α or γ); wortmannin by contrast displayed activity in the same general potency range as the most selective compound tested (55-147 nM) but with a pan-isoform profile.

Example 9

Figure 3:
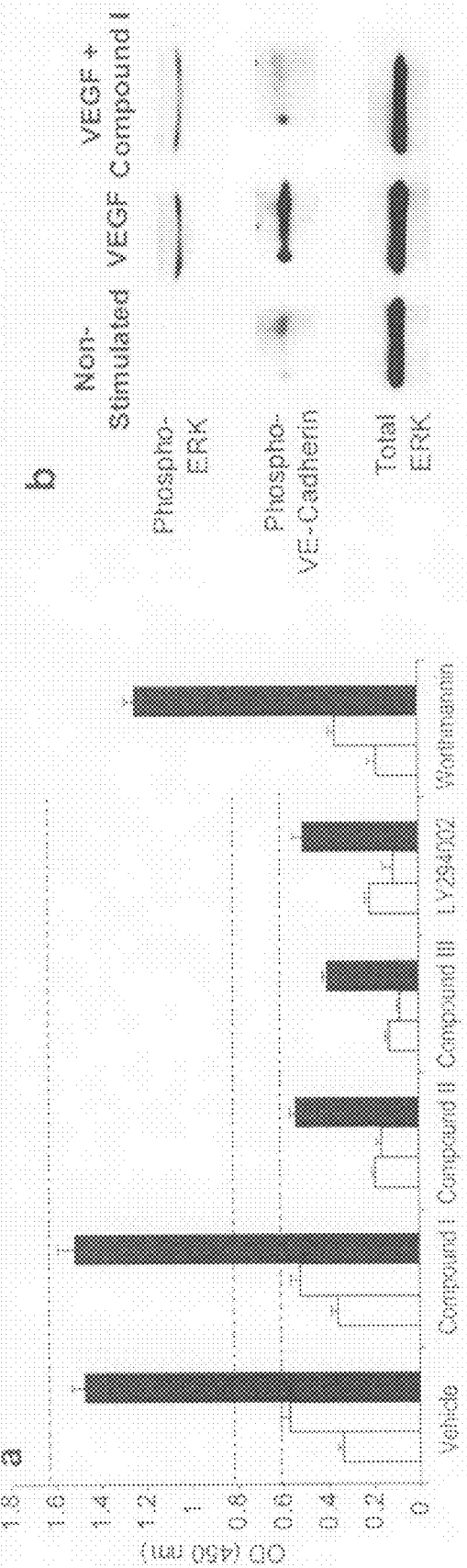
FIG. 3. Inhibition of cell proliferation and signaling. (a) EC were cultured in the presence of vehicle (DMSO) or PI3K inhibitors (all at 10 µM); cell proliferation was assessed either 24 (open bar), 48 (grey bar), or 72 h (black bar) later. Data presented as OD at 450 nm (mean±SEM, n=6; at all time-points, vehicle and Compound I groups differ from all others but not each other by P<0.001). (b) EC were cultured in either serum-free medium (non-stimulated), medium with added VEGF, or medium with VEGF plus 10 uM Compound I. Cell lysates were then processed for Western blot analyses to detect phosphorylated VE-cadherin or ERK1/2, or total ERK2 (as a loading control).

PI3Kγ/δ inhibition selectively impacts growth factor signaling. PI3K isoforms can differently regulate cellular processes, as with mitogenesis falling under PI3Kα and β control. Applicants therefore compared the compounds profiled in Table 1 for their effects on cell proliferation. As expected, pan-isoform inhibitors (Compound II and wortmannin) strongly inhibited EC proliferation (FIG. 3a). Compound II and LY294002 displayed similar efficacy, suggesting that either PI3Kα and β inhibition is sufficient for blocking mitogenesis. Compound I, by contrast, had no effects on EC proliferation even at relatively high concentrations (up to 10 uM). Additionally, these compounds did not block VEGF-induced angiogenesis in vivo (using a Matrigel implant model, data not shown). In agreement with these data, Compound I was also found to have no influence on VEGF-stimulated ERK phosphorylation (FIG. 3b), a signaling event in this growth factor's mitogenic pathway. It did, however, interrupt other VEGF signaling pathways, such as those that culminate in VE-cadherin phosphorylation, the culmination of a signaling cascade that underlies VEGF's pro-edema activity. These data indicate that while the non-ERK-related pathway(s) leading to VE-cadherin phosphorylation are dependent upon intact PI3Kγ and/or δ activity, those that control cell proliferation are not Example 10

Figure 4:
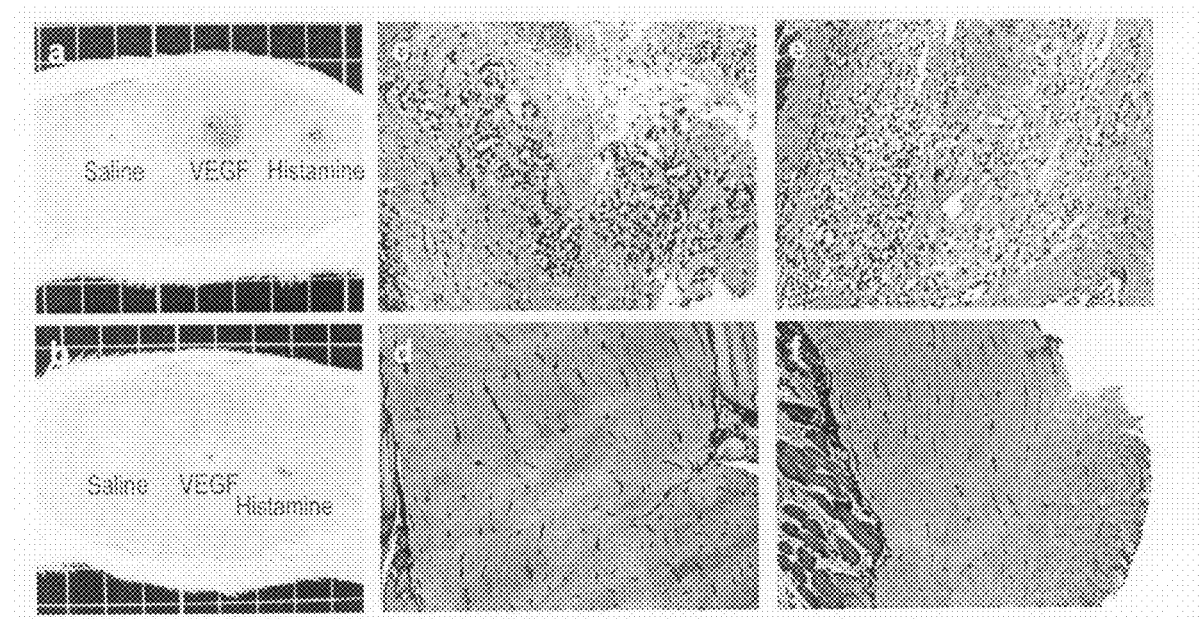
FIG. 4. Inhibition of edema and inflammation. (a, b) Rats were injected i.v. with Evans blue dye and then intradermally with saline, VEGF or histamine. Pretreatment with Compound I (1 mg/kg) (b) reduced edema formation relative to vehicle-treated animals (a). (c-f) Rat hindpaws were injected with either PAF (c & d) or dextran (e & f), and three hours later processed as H&E-stained paraffin sections. Pretreatment with Compound I (d & f; 5 mg/kg) blocked both the edema and leukocytic infiltrate induced by these two inflammatory mediators relative to animals dosed with vehicle alone (c & e). Images were taken of paws representing the mean group value for volume as presented in Results (original magnification 200×).

PI3Kγ/δ inhibition reduces edema and inflammation in vivo. As VE-cadherin phosphorylation triggers a reduction in endothelial barrier function, the ability of Compound I to block this event should translate into an anti-edema effect. This was directly demonstrated in Miles assay studies, where this compound inhibited VEGF-induced vascular permeability (FIGS. 4a & b). Compound I also blocked histamine-induced permeability, as predicted based on PI3K's role in GPCR signaling. Varying the time between compound administration and agonist challenge demonstrated that a single i.v. administration reduced edema formation for at least 4 hours. (data not shown).

Figure 5:
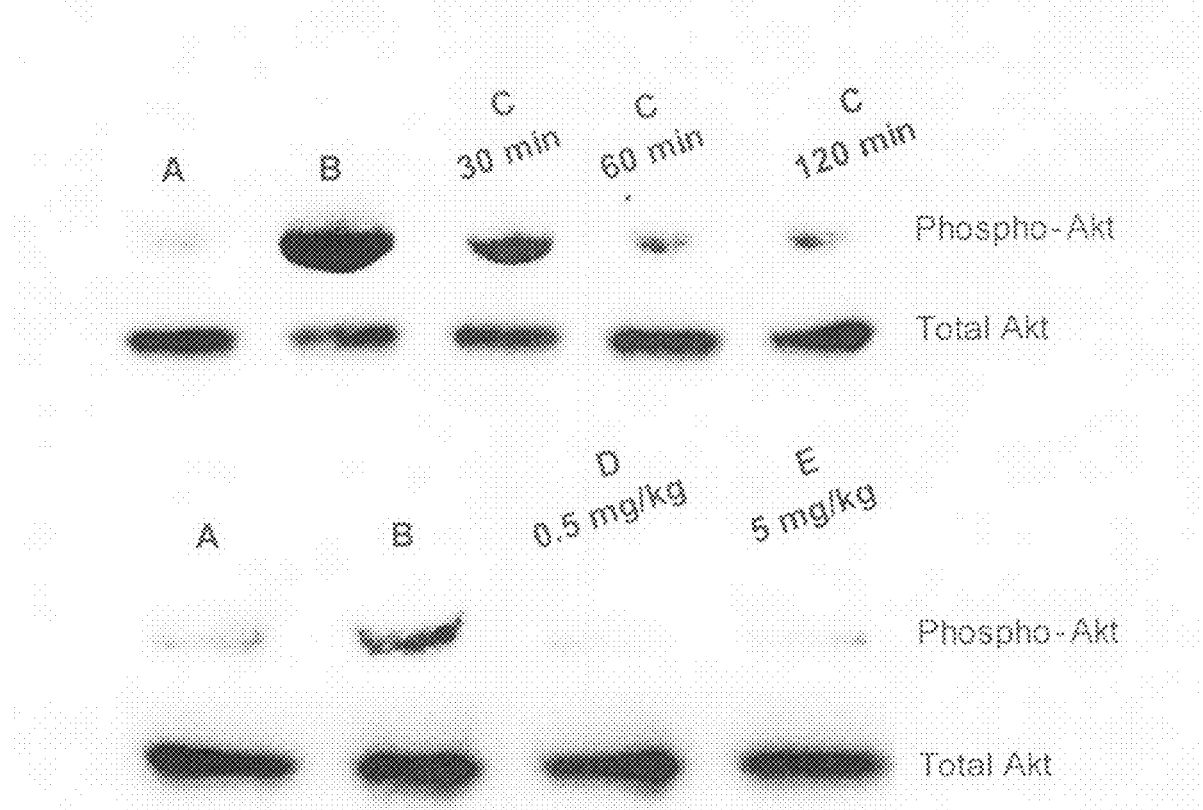
FIG. 5. Inhibition of VEGF-induced Akt phosphorylation in vivo. Rats were first injected i.v. with either vehicle or Compound I (0.5 mg/kg in the upper panel, 0.5 or 5 mg/kg in the lower), followed by either VEGF (20 ng) or saline; timing of the second injection was 30-120 min later in the upper panel, 60 min in the lower. Lungs were explanted 5 min after VEGF or saline injection, processed to tissue lysates, and lysates probed in Western blots to detect either phosphorylated Akt or total Akt (as a loading control).

The Miles assay models a primarily endothelial-based response that develops rapidly (within minutes). As a comparator, we next employed a rodent hindpaw model where more complex inflammatory reactions develop over several hours. Agonists included PAF, a GPCR ligand that activates both EC and leukocytes, and dextran, a phagocytic stimulus for mast cell and leukocyte activation. Histology revealed quite clearly that Compound I strongly antagonized both the edema and leukocyte infiltration induced by these two mediators (FIG. 4c-f). Paw volume (a more quantitative measure of edema and inflammation) was reduced by 62% and 78% in response to PAF or dextran, respectively (n=8, P<0.001). Finally, to correlate these in vivo responses with the molecular target of interest, we monitored PI3K pathway signaling through Western blot analyses of Akt phosphorylation (a PI3K-mediated event). Intravenous VEGF injection in mice induced a rapid Akt phosphorylation readily detectable in lung lysates, and as expected pretreatment with Compound I blocked this response (FIG. 5, see Supporting Information). Blockade was seen with Compound I doses as low as 0.5 mg/kg and persisted over a several hour period.

Example 11

Figure 6:
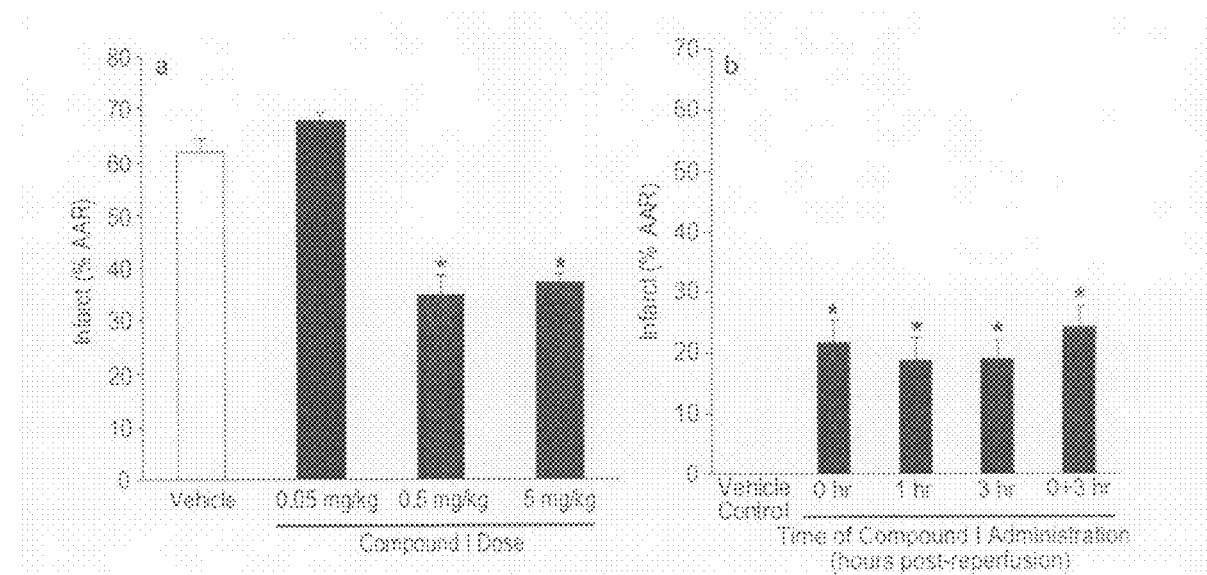
FIG. 6. Reduction of infarct development in a rodent MI model. (a) Rats were subjected to 60 min of LAD occlusion followed by vehicle or Compound I delivery (at the indicated dose) 60 min post-reperfusion. Both ischemic area (AAR) and infarct area were then determined 24 h post-study initiation. Data shown as infarct area as a percentage of the AAR (means±SEM, n=6; *, 0.5 and 5 mg/kg Compound I dose groups differ from vehicle control by $P<0.05$ but not from one another). (b) Animals were treated as in Panel a except that a single Compound I dose (0.1 mg/kg) was delivered from 0 h to 3 h post-reperfusion; in one group animals were dosed at 15 both 0 and 3 h. Data shown as in (a) (n=5-9; *, all Compound I groups differ from vehicle control by $P<0.001$ but not from one another).

PI3Kγ/δ inhibition limits infarct development and improves myocardial functioning in rodents. Applicants previously documented in rodents the vascular changes, such as edema and neutrophil activation, which contribute to infarct development. Given the anti-inflammatory actions of our PI3Kγ/δ inhibitors therefore, applicants tested compounds for possible cardioprotective activities. In a rodent model of MI, Compound I delivered as a single i.v. bolus 60 mm post-reperfusion routinely reduced infarct size by 40% or more, with maximal efficacy reached by a dose of 0.5 mg/kg (FIG. 6a). (This model initiates with a 60 mm coronary artery occlusion followed by complete reperfusion and then infarct measurement at 24 h; in control animals the ischemic zone typically covers 30-45% of the total left ventricle [LV] with 55-70% infarction of this area. Pilot studies revealed that longer ischemic periods do not produce larger infarcts and that infarcts do not reach a fixed size until approximately 6 h post-reperfusion). Immunohistochemistry as well as EM revealed similar patterns of monocyte and neutrophil infiltration in hearts from Compound I vs. vehicle-treated animals. While it was obvious that infarcts were smaller in animals treated with Compound I, inflammatory infiltrates were present to an equivalent degree in infarcted myocardium from both treatment groups; inflammation was not detectable, by contrast, in viable tissue (i.e., myocardium not showing morphologic signs of cardiomyocyte or vascular damage)

These observations are consistent, therefore, with an action by selective PI3Kγ/δ inhibiting Compound I highly to reduce the overall area in which inflammation occurs, and thus the final extent of infarction. To better define the available therapeutic window for this cardioprotective effect, the most highly selective invention compound was administered at various times during the reperfusion period (FIG. 6b). Delivery between 0 and 3 h post-reperfusion produced statistically significant but equivalent reductions in infarct development (in this case 58-67% reductions vs. vehicle-treated controls). Repeat dosing at both 0 and 3 h also provided equivalent efficacy, suggesting that a single administration is sufficient for maximal efficacy. Finally, to confirm the functional benefit of infarct reduction, myocardial contractility was assessed by echocardiography 4 weeks after infarct induction. The percent left ventricular long axis fractional shortening observed in animals that had received vehicle placebo was 27.2±1.9 (mean±SEM), whereas animals dosed with the most selective compound as a single 0.5 mg/kg bolus one hour post-reperfusion had a 24% improvement in this measure (33.6±2.0, n=12-13, P=0.03). These data therefore confirm a long-lasting functional benefit to PI3Kγ/δ inhibition during myocardial reperfusion injury.

Example 12

Figure 7:
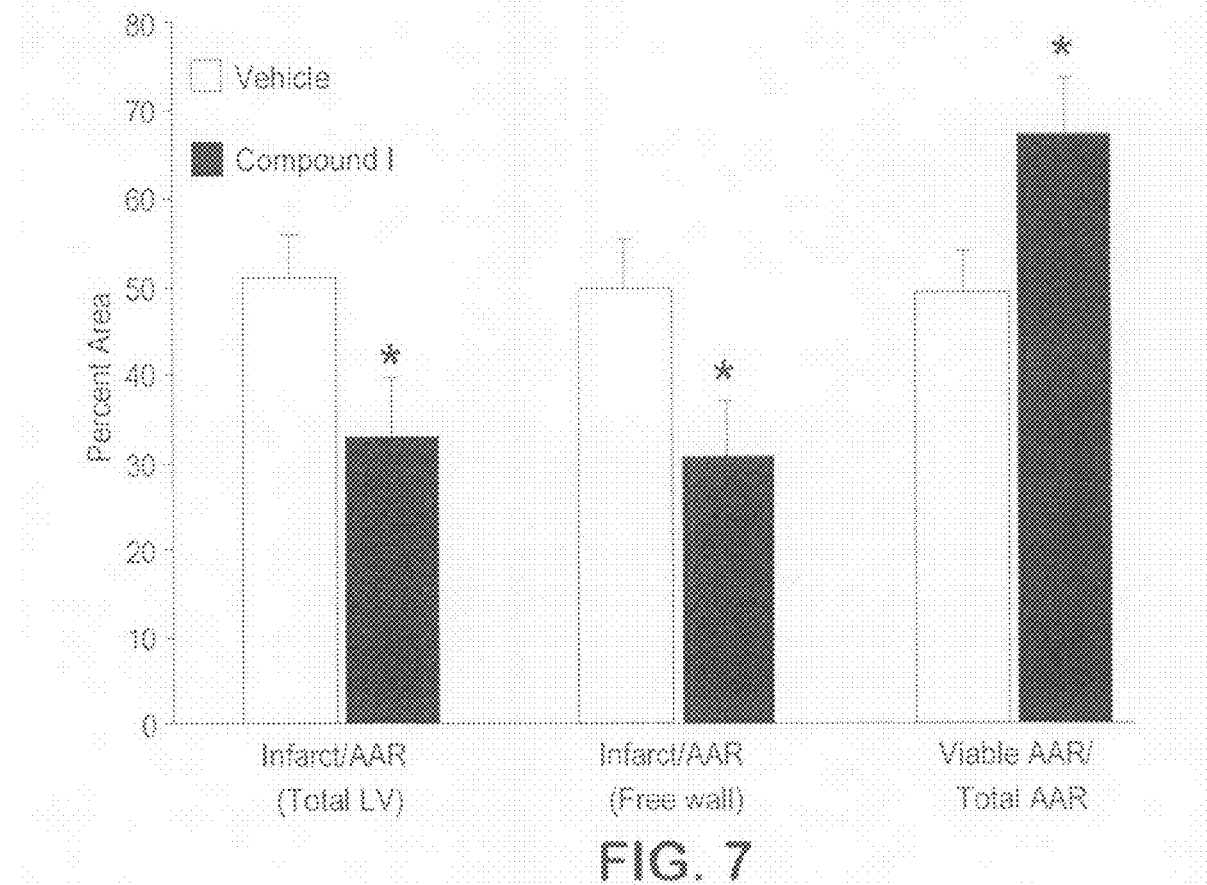
FIG. 7. Reduction of infarct development in a porcine MI model. Pigs were subjected to 90 min of LAD occlusion followed by vehicle or invention compound (0.5 mg/kg) delivery 30 min post-reperfusion. At 24 h post-study initiation, total ischemic area (AAR), viable AAR and infarcted AAR were determined, for both the entire left ventricle (LV) as well as the free wall alone. Data shown as infarct as a percentage of AAR, or viable AAR as a percentage of total AAR (means±SEM, n=12-13; *, vehicle and invention compound groups differ for all measures by $P \leq 0.04$).

PI3Kγ/δ inhibition limits infarct development in a porcine MI model. In a final series of studies, MIs were modeled in the pig, as this species better approximates human coronary anatomy and responses to myocardial I/R injury. With aggressive model parameters of a 90 min ischemic period, therapeutic dosing 30 min post-reperfusion and infarct measurement at 24 h, we typically observed ischemic zones representing 20-30% of the total LV and 20-30% infarction of this area in control animals. In initial dose-ranging studies, generally equivalent responses were observed using doses of 0.5-mg/kg of Compound I, and we therefore elected to conduct a statistically-powered test at the lowest dose. Animals dosed with Compound I as a single 0.5 mg/kg i.v. bolus 30 min post-reperfusion developed smaller infarcts vs. vehicle-treated controls (FIG. 7). Measuring infarct area as percent of total LV ischemic area, infarct size was reduced by 35% (P=0.04). Viable tissue within the ischemic zone was increased by 37% (P=0.04), directly demonstrating the cardioprotective effect of PI3Kγ/δ inhibition. Finally, taking advantage of the larger porcine heart to make more detailed measurements, infarct areas within the LV free wall only (as opposed to the free plus attached wall measurements reported up to this point) were also determined, reasoning that free wall infarcts are of greatest relevance to overall myocardial function. As anticipated, Compound I reduced free wall infarct size by 38% vs. vehicle-treated controls (P=0.05).

Example 13

Inhibition of VEGF-Induced Edema

Miles Assay Data

A rodent model of vascular edema, the Miles assay, was used to screen compounds for their ability to inhibit VEGF-induced edema. The table below presents several examples drawn from these studies, in which compounds cited in this application successfully inhibited edema formation.

| Treatment | Dose (mg/kg BW) | Score (scale of 0-12) |
|---|---|---|
| Vehicle | | 12 |
| 4-{[(2,4-Diamino-pteridin-6-ylmethyl)-amino]-methyl}-benzene-1,2-diol | 5 mg/kg | 4 |
| 4-(2,4-Diamino-pteridin-6-yl)-phenol (sulfate salt) | 5 mg/kg | 2 |
| 2-[2-(1H-Indol-2-yl)-phenyl]-isoindole-1,3-dione | 1.5 mg/kg | 3 |
| | 1.5 mg/kg | 3 |
| 6,7-Bis-(3-hydroxy-phenyl)-pteridine-2,4-diol | 1.5 mg/kg | 3 |
| 3-(4-Hydroxy-phenyl)-N-[2-(1H-indol-2-yl)-phenyl]-propionamide | 1.5 mg/kg | 2 |
| 2-(4-Hydroxy-phenyl)-N-[2-(1H-indol-2-yl)-phenyl]-acetamide | 1.5 mg/kg | 2 |
| 2-(3,4-Dihydroxy-phenyl)-N-[2-(1H-indol-2-yl)-phenyl]-acetamide | 0.5 mg/kg | 7 |
| N-[2-(2,3-Dihydro-1H-indol-2-yl)-phenyl]-2-hydroxy-benzamide | 0.5 mg/kg | 5 |
| 3-[2-(1H-Indol-2-yl)-phenylcarbamoyl]-pyridine-2-carboxylic acid | 0.5 mg/kg | 5 |
| 2-Hydroxy-5-(6-phenyl-pteridin-4-ylamino)-benzenesulfonic acid | 0.5 mg/kg | 6 |
| 5-(6-Phenyl-pteridin-4-ylamino)-quinolin-8-ol hydrochloride salt | 0.5 mg/kg | 5 |
| 3,4-Dihydroxy-N-[2-(1H-indol-2-yl)-phenyl]-benzamide | 0.1 mg/kg | 6 |
| 6-{[(Pyridin-2-ylmethyl)-amino]-methyl}-pteridine-2,4-diamine | 0.1 mg/kg | 4 |
| 6-{[(Naphthalen-2-ylmethyl)-amino]-methyl}-pteridine-2,4-diamine | 0.1 mg/kg | 4 |
| 2,3-(3,4-Dihydroxyphenyl)-pyrido[3,4-b]pyrazin-8-ylamine | 0.01 mg/kg | 6 |
| 3-[2,4-diamino-6-(3-hydroxyphenyl)pteridin-7-yl] phenol dihydrochloride salt | 1 mg/kg | 4 |
| 3-[2,4-diamino-6-(3-hydroxyphenyl)pteridin-7-yl] phenol dihydrochloride salt | 0.1 mg/kg | 4 |
| 3-[2,4-diamino-6-(3-hydroxyphenyl)pteridin-7-yl] phenol dihydrochloride salt | 0.01 mg/kg | 3 |
| 4-[4-amino-6-(3,4-dihydroxyphenyl)pteridin-7-yl]benzene-1,2-diol chloride salt | 1 mg/kg | 5 |
| 4-[4-amino-6-(3,4-dihydroxyphenyl)pteridin-7-yl]benzene-1,2-diol chloride salt | 0.1 mg/kg | 3 |
| 4-[4-amino-6-(3,4-dihydroxyphenyl)pteridin-7-yl]benzene-1,2-diol chloride salt | 0.01 mg/kg | 6 |

Sprague-Dawley rats were first injected IV with vehicle alone or test agent, followed by IV injection of Evans blue dye, followed by intradermal injections of saline and VEGF (200 ng/injection site) along both shaved flanks. After 45 min, intradermal injection sites were photographed and then scored by a blinded observer for extravasation of Evans blue dye into the dermis (dermal bluing) according to a 4 point scoring system (3=maximal bluing, >75% of response in vehicle-treated animals; 2=medium bluing, >25% but <75% of vehicle-treated animals; 1=minimal bluing, <25% of vehicle-treated animals; 0=bluing equivalent to saline injection sites on same animal). Individual scores for 4 injection sites (from 2 separate animals) were summed and are shown as a scale of 0-12, with a lower score indicating the greater anti-edema activity; note that all vehicle-treated groups score a value of 12, based on the scoring system outlined above.

The ability of test agents to influence edema induced by agonists other than VEGF was also tested. Compounds cited in this application inhibited edema formation induced using histamine as an agonist, for example, as shown below.

| Treatment | Dose (mg/kg BW) | Score with VEGF as agonist (scale of 0-12) | Score with histamine as agonist (scale of 0-12) |
|---|---|---|---|
| Vehicle | | 12 | 12 |
| 6,7-bis(4-hydroxyphenyl)-pteridin-4-ylamine sulfate salt | 1.5 mg/kg | 4 | 3 |
| 6,7-Diphenyl-pteridin-4-ol | 1.5 mg/kg | 3 | 4 |
| 3,4,5-Trihydroxy-N-[2-(1H-indol-2-yl)-phenyl]-benzamide | 1.5 mg/kg | 4 | 7 |
| 3,4,5-Trihydroxy-N-(1H-indol-2-yl)-benzamide | 1.5 mg/kg | 5 | 7 |

The ability of test agent to influence vascular edema was tested as above, except that the ability to block edema was tested using either VEGF or histamine as the agonist (200 ng and 10 μg/injection site, respectively).

Example 14

Reduction of Myocardial Infarction

Myocardial Infarct Data

A rodent model of acute myocardial infarct, in which the proximal left anterior descending coronary artery (LAD) is occluded for 60 min followed by reperfusion, was used to determine whether test agents reduced infarct size at 24 hours. Several examples of the compounds cited in this application significantly reduced infarct size as compared to controls.

| Study # | Treatment | Dose (mg/kg BW) | Infarct (% AAR, mean ± SEM) | % Infarct reduction |
|---|---|---|---|---|
| 1 | Vehicle | | 75.9 ± 1.8 | |
| | 6,7-bis(4-hydroxyphenyl)-pteridin-4-ylamine sulfate salt | 1.5 | 60.6 ± 1.8 | 20% |
| 2 | Vehicle | | 54.0 ± 2.9 | |
| | 6,7-bis(3,4-dihydroxyphenyl)-pteridine-2,4,-diamine, hydrochloride salt | 1.5 | 36.3 ± 6.3 | 33% |
| 3 | Vehicle | | 54.0 ± 2.9 | |
| | 3-[2,4-diamino-6-(3-hydroxyphenyl)pteridin-7-yl] phenol dihydrochloride salt | 1.0 | 46.4 ± 2.6 | Not significant |

-continued

| Study # | Treatment | Dose (mg/kg BW) | Infarct (% AAR, mean ± SEM) | % Infarct reduction |
|---|---|---|---|---|
| | 3-[2,4-diamino-6-(3-hydroxyphenyl)pteridin-7-yl] phenol dihydrochloride salt | 0.1 | 37.7 ± 5.8 | 30% |
| 4 | Vehicle | | 61.9 ± 3.1 | |
| | 4-[4-amino-6-(3,4-dihydroxyphenyl)pteridin-7-yl]benzene-1,2-diol chloride salt | 1.0 mg/kg | 40.1 ± 2.0 | 35% |
| | 4-[4-amino-6-(3,4-dihydroxyphenyl)pteridin-7-yl]benzene-1,2-diol chloride salt | 0.1 mg/kg | 37.1 ± 2.6 | 40% |
| | 6,7-Bis(3-hydroxyphenyl)-pteridine-4-ylamine hydrochloride salt | 1.0 mg/kg | 39.1 ± 7.5 | 37% |
| | 6,7-Bis(3-hydroxyphenyl)-pteridine-4-ylamine hydrochloride salt | 0.1 mg/kg | 39.1 ± 4.2 | 37% |
| 5 | Vehicle | | 54.9 ± 3.1 | |
| | 3-[2,4-Diamino-6-(3-hydroxyphenyl)pteridin-7-yl]phenol dibromide salt | 0.5 mg/kg | 31.6 ± 6.2 | 42% |
| | 6,7-bis(3-hydroxyphenyl)-pteridine-2,4-diamine (PF1) | 0.5 mg/kg | 37.8 ± 4.5 | 31% |
| | 6,7-bis(3-hydroxyphenyl)-pteridine-2,4-diamine (PF2) | 0.5 mg/kg | 35.4 ± 1.8 | 35% |
| | 6,7-bis(3-hydroxyphenyl)-pteridine-2,4-diamine (PF5) | 0.5 mg/kg | 38.7 ± 5.3 | 29% |

Myocardial infarcts were created in Sprague-Dawley rats (200-300 g body weight) by a 60 min occlusion of the LAD followed by LAD reperfusion. At 90 min post-reperfusion, either vehicle alone or test agents were injected IV. At 24 hr post-treatment, the ischemic zone (area at-risk, AAR) was delineated by re-ligation of the LAD followed by IV injection of alkali blue dye, after which hearts were sectioned along the short axis and stained using triphenyltetrazolium chloride to delineate viable from infarcted myocardium. Photographic images were then analyzed using morphometric software to calculate infarct area as a percent of the at-risk area.

Study 1: Group sizes N=5-6; 6,7-bis(4-hydroxyphenyl)-pteridin-4-ylamine sulfate salt differs from vehicle control (P<0.0005).

Study 2: Group sizes N=5; 6,7-bis(3,4-dihydroxyphenyl)-pteridine-2,4-diamine hydrochloride salt differs from vehicle control (P<0.035).

Study 3: Group sizes N=3-5; 3-[2,4-diamino-6-(3-hydroxyphenyl)pteridin-7-yl]phenol dihydrochloride salt at 0.1 mg/kg differs from vehicle control (P<0.03).

Study 4: Group sizes N=4-5; all 4-[4-amino-6-(3,4-dihydroxyphenyl)pteridin-7-yl]benzene-1,2-diol chloride salt and 6,7-Bis(3-hydroxyphenyl)-pteridine-4-ylamine hydrochloride salt treatment groups differ from vehicle control (P<0.02).

Study 5: 3-[2,4-Diamino-6-(3-hydroxyphenyl)pteridin-7-yl]phenol dibromide salt was delivered in 8% PEG400 (Vehicle), while 6,7-Bis(3-hydroxyphenyl)-pteridine-2,4-diamine was delivered as one of three product formulations (PF1=2.8% hydroxypropyl-θ-cyclodextrin, 1.84% PEG400, and 0.009% EDTA in 20 mM pH 3 citrate buffer; PF2=1.8% hydroxypropyl-θ-cyclodextrin and 0.06% polyvinylpyrrolidone in 20 mM pH 3 citrate buffer; PF3=0.8% sulfonbutyl ether-θ-cyclodextrin and 0.03% polyvinylpyrrolidone in 20 mM pH 3 citrate buffer). Group sizes N=5-6; all treatment groups differ from vehicle control (P<0.05).

The following studies were performed as described above, except that the timing of 3-[2,4-diamino-6-(3-hydroxyphenyl)pteridin-7-yl]phenol dihydrochloride salt administration (at 0.1 mg/kg) was varied. In one group, 3-[2,4-diamino-6-(3-hydroxyphenyl)pteridin-7-yl]phenol dihydrochloride salt was administered at both 60 and 240 min post-occlusion.

| Study | Treatment | Administration time (min post-occlusion) | Infarct (% AAR, mean ± SEM) | % Infarct reduction |
|---|---|---|---|---|
| 1 | Vehicle | 60 | 54.0 ± 2.9 | |
| | 3-[2,4-diamino-6-(3-hydroxyphenyl)pteridin-7-yl] phenol dihydrochloride salt | 60 | 21.6 ± 5.7 | 60% |
| | 3-[2,4-diamino-6-(3-hydroxyphenyl)pteridin-7-yl] phenol dihydrochloride salt | 120 | 18.8 ± 5.6 | 65% |
| | 3-[2,4-diamino-6-(3-hydroxyphenyl)pteridin-7-yl] phenol dihydrochloride salt | 240 | 19.1 ± 4.0 | 65% |
| | 3-[2,4-diamino-6-(3-hydroxyphenyl)pteridin-7-yl] phenol dihydrochloride salt | 60 and 240 | 24.2 ± 4.9 | 55% |

Group sizes N=4-5; all 3-[2,4-diamino-6-(3-hydroxyphenyl)pteridin-7-yl]phenol dihydrochloride salt treatment groups differ from vehicle control (P<0.001).

To model myocardial infarction (MI) in rats, transient ischemia was induced by a 60 min LAD occlusion, and then 60 min into the reperfusion period Compound I was delivered IV as a one-time bolus; at 24 hr infarct area was measured using morphometric techniques and represented as the percentage of ischemic territory. Maximal efficacy of Compound I was reached by a dose of 0.3 mg/kg, with a 43% reduction in infarct size vs. vehicle controls (35%±9 vs. 62%±7, mean±SD, N=8, P<0.001). Equivalent infarct reductions were seen when dosing immediately at reperfusion or out to 3 hr later. In a porcine MI model (90 min of LAD occlusion followed by complete reperfusion), a single 0.3 mg/kg IV bolus delivered 30 min post-reperfusion reduced infarct size by 32% vs. controls (40% vs. 56%, N=12-13, P=0.03).

Example 15

Stroke Data

A rodent model of cerebral stroke, in which the middle cerebral artery is permanently occluded, was used to determine whether test agents reduced infarct size at 24 hours. Several examples of the compounds cited in this application significantly reduced infarct size as compared to controls, and to a greater degree than two commercially available compounds (PP1 and SU6656) described in the literature as Src kinase inhibitors.

| Study # | Treatment | Infarct area in mm$^3$ (mean ± SEM) | % Infarct reduction |
|---|---|---|---|
| 1 | Vehicle | 42.4 ± 6.25 | — |
|   | PP1 | 35.4 ± 6.4 | Not significant |
|   | SU6656 | 24.3 ± 5.3 | Not significant |
|   | 6,7-Di-pyridin-2-yl-pteridin-4-ylamine | 27.2 ± 2.63 | Not significant |
|   | 6,7-Diphenyl-pteridine-2,4-diol | 20.2 ± 4.19 | 52% |
|   | N-(2-(1H-Indol-2-yl)-phenyl)-phthalamic acid | 15.6 ± 5.16 | 63% |
| 2 | Vehicle | 39.0 ± 5.0 | — |
|   | 6,7-bis(4-hydroxyphenyl)-pteridin-4-ylamine, sulfate salt | 18.3 ± 2.6 | 53% |

Cerebral strokes were created in mice by permanent ligation of the middle cerebral artery using a cauterizing tool, followed 60 min later by IV injection of either vehicle alone (50% PEG400 in water) or test agents (at 1 mg/kg BW). Twenty four hours later, brains were sectioned and stained using triphenyltetrazolium chloride to delineate viable from infarcted tissue. Photographic images were then analyzed using morphometric software to calculate infarct area.

Study 1: Group sizes N=5-6; the 6,7-diphenyl-pteridine-2,4-diol and N-(2-(1H-indol-2-yl)-phenyl)-phthalamic acid groups differ from vehicle control (P<0.05 and P<0.01, respectively).

Study 2: Group sizes N=6-7; the 6,7-bis(4-hydroxyphenyl)-pteridin-4-ylamine, sulfate salt group differs from vehicle control (P<0.006).

Example 16

Inhibition of PI3 Kinase

The ability of compounds to inhibit the activity of PI3K kinase was determined using biochemical assays. In a first assay, compounds were tested at two concentrations (0.5 and 5 µM) for their ability to inhibit enzymatic activity of the human p120γ subunit of PI3K (the assay being performed under contract by Upstate Group, Charlottesville, Va.). Data are expressed as percent control (where 100% represents no inhibition and 0% represents complete inhibition of enzymatic activity):

| Compound | Percent Control Value at 0.5 µM | Percent Control Value at 5 µM |
|---|---|---|
| 6,7-Diphenyl-pteridine-2,4-diamine | 101 | 81 |
| 2-Amino-6,7-bis-(3-hydroxyphenyl)-pteridin-4-ol | 102 | 99 |
| 6,7-Bis(4-hydroxyphenyl)-pteridine-4-ylamine | 102 | 85 |
| 4,4'-(2,4-diaminopteridine-6,7-diyl)dibenzene-1,2-diol | 66 | 12 |
| Compound I | 47 | 5 |
| 2,3-Bis(4-hydroxyphenyl)-pyrido[3,4-b]pyrazin-8-ylamine | 101 | 94 |
| 3,3'-(8-aminopyrido[3,4-]pyrazine-2,3-diyl)diphenol | 101 | 90 |
| 6,7-Bis(3-hydroxyphenyl)-pteridine-4-ylamine | 97 | 71 |
| 6,7-Bis(4-hydroxyphenyl)-pteridine-2,4-diamine | 94 | 46 |

In a second assay, compounds were tested at multiple input concentrations for inhibition of p120γ in order to generate inhibition curves and calculate IC$_{50}$ values (the compound concentration at which enzyme activity is inhibited to 50% of control value):

| Compound | IC$_{50}$ Value |
|---|---|
| 2-Amino-6,7-bis-(3-hydroxyphenyl)-pteridin-4-ol | 48 µM |
| 4,4'-(2,4-diaminopteridine-6,7-diyl)dibenzene-1,2-diol | 273 nM |
| 4-[4-amino-6-(3,4-dihydroxyphenyl)pteridin-7-yl]benzene-1,2-diol | 968 nM |
| Compound I | 83 nM |
| 6,7-Bis(3-hydroxyphenyl)-pteridine-4-ylamine | 3.9 µM |
| 3-(2,4-Diamno-pteridin-6-yl)-phenol | 50 nM |

In a third assay, IC$_{50}$ values were determined against the human p110β and p110δ subunits of PI3K:

| Compound | IC$_{50}$ Value Determined Against p110β | IC$_{50}$ Value Determined Against p110δ |
|---|---|---|
| Compound I | 1.2 µM | 235 nM |
| 3-(2,4-Diamino-pteridin-6-yl)-phenol | 215 nM | 24 nM |

The IC$_{50}$ value for compounds were determined using a luminescence-based kinase assay with recombinant phosphatidylinositol 3-kinase-p120γ (PI3K) obtained from Upstate Cell Signaling Solutions. In white, flat-bottom, 96-well plates (Nunc) parallel assays were run at room temperature at a final volume of 50 µL. Each well contained 40 µL of buffer consisting of 20 mM Tris buffer, pH 7.4, containing 4 mM MgCl$_2$, 10 mM NaCl, 50 µM D-myo-phosphatidylinositol 4,5-bisphosphate substrate (Echelon Biosciences, Inc.) and an appropriate amount of PI3-K (250-500 ng/well) such that the assay was linear over 90 min. The final concentration of compounds for IC$_{50}$ value determinations ranged from 100 to 0.001 µM by adding the appropriate amount of compound in 2.5 µL of DMSO; the DMSO present in each assay was constant at 5%. The reaction was initiated by the addition of 10 µL of ATP to a final assay concentration of 3 µM. After the reaction was to proceed for 90 min, 50 µL of Kinase-Glo reagent (Promega) was added to terminate the reaction. This solution was then allowed to proceed for an additional 10 min to maximize the luminescence reaction. Values were then measured using an Ultra 384 instrument (Tecan) set for luminosity measurements. Two control reactions were also ran: one containing no compound and the second containing neither compound nor the phosphatidylinositol 4,5-bisphosphate substrate. Data from four wells were then averaged and used to determine $IC_{50}$ values for the test compounds. $IC_{50}$ values were derived from experimental data using the non-linear curve fitting capabilities of Prism (Version 4; GraphPad Software).

The ability of compounds to impact PI3K activity in vivo was assessed by examining compound influence on vascular endothelial growth factor (VEGF)-induced Akt kinase phosphorylation (VEGF stimulation being an inducer of PI3K activity, and Akt kinase being a direct target of PI3K). Sprague Dawley rats were first injected intravenously (iv) with either vehicle or test compound at 5 mg/kg, and then 30, 60 or 120 min later injected iv with VEGF. Five minutes later, lungs were harvested and used to generate tissue lysates, which were then probed for phosphorylated Akt using Western blot technology; non-phosphorylated Akt was also probed in the same blots as a loading control. In other studies, test compounds was dosed at either 0.5 or 5 mg/kg, and VEGF delivered 60 min later, in order to assess the dose-response relationship of a compound's activities. Inhibition of VEGF-induced Akt phosphorylation was seen at all time-points examined (30, 60, and 120 min) following 6,7-bis-(3-hydroxyphenyl)-pteridine-2,4-diamine delivery, and at all 6,7-bis-(3-hydroxyphenyl)-pteridine-2,4-diamine doses examined (0.5 and 5 mg/kg).

Example 17

Reduction of Inflammation

In order to determine the influence of compounds on the development of inflammation, Sprague Dawley rats were first injected intravenously with either vehicle or test compound at 5 mg/kg, and then 30 min later either PBS (as a control), dextran or platelet activating factor (PAF) was injected into the plantar surface of the hindlimbs, dextran and PAF being known to induce localized inflammatory responses marked by edema. Three hours later, paw dimensions were measured using a caliper and paw volumes calculated; data are shown as the increase in paw volume ($mm^3$) as compared to controls (paws injected with PBS). As shown in the table below, dextran and PAF-induced inflammatory edema were demonstrable as increases in paw volume, and 6,7-bis-(3-hydroxyphenyl)-pteridine-2,4-diamine (delivered at 5 mg/kg) blocked these responses. Data are shown as means±SEM (N=6); vehicle and 6,7-bis-(3-hydroxyphenyl)-pteridine-2,4-diamine groups differ by P<0.001.

| Compound Pretreatment | Inflammatory Stimulus | Increase in Paw Volume vs. Controls ($mm^3$) |
|---|---|---|
| Vehicle | Dextran | 148 ± 6 |
| Compound I | Dextran | 32 ± 5 |
| Vehicle | PAF | 71 ± 9 |
| Compound I | PAF | 27 ± 4 |

Example 18

Preparation of Pharmaceutical Composition of Compound I

To a vessel containing 6,670 g of sterile water for injection (SWFI), was added 3,680 g Captisol (a sulfobutyl ether derivative of β-cyclodextrin), with stirring. Following cyclodextrin dissolution, 540.2 g Compound I was added with stirring and the pH was adjusted to about 1.2 using 5 N hydrochloric acid. Following dissolution of Compound I, 82.1 g citric acid was added, and following citric acid dissolution, an additional 9,154 g of SWFI was added. The pH was adjusted to between about 2.9 and 3.0, using 2 N sodium hydroxide.

Following adjustment with SWFI so as to achieve final concentrations of about 74 mM cyclodextrin, about 68 mM Compound I, and about 20 mM citric acid, the final formulation was passed through a 0.2 µM sterile filter, aliquoted to vials, and lyophilized. The final composition contained about 21,595 g SWFI. For final use, lyophiles were reconstituted with SWFI.

After reconstituting the lyophilized material, the final formulation was used for treatment of a patient in need of such treatment. The formulation used for the treatment included 23 mg/ml Compound I and 16% Captisol (w:w); the dose delivered to the patient can be, for example, depending on volume delivered, between about 0.04 mg/kg and 5 mg/kg.

Example 19

In Vitro and In Vivo Assay Preparations

Kinase assays: For PI3K assays, 40 µL reaction buffer (20 mM Tris, 4 mM $MgCl_2$, 10 mM NaCl, pH 7.4) containing 50 µM D-myo-phosphatidylinositol 4,5-bisphosphate substrate (Echelon Biosciences, Salt Lake City, Utah) and the desired PI3K isoform (Upstate USA, Charlottesville, Va.) were aliquoted to 96 well plates; kinase concentrations were 250-500 ng/well, such that linear kinetics were achieved over 90 min. The compound to be tested was then added as 2.5 µL of a DMSO stock to final concentration range of 100 µM. to 1 nM. Reactions were initiated by addition of 10 µL of ATP to a final concentration of 3 µM, and after 90 min 50 µL of Kinase-Glo reagent (Promega, Madison, Wis.) added to quantify residual ATP levels; luminosity was measured using an Ultra 384 instrument (Tecan, Durham, N.C.). Control reactions omitting either test compound or substrate were also performed. $IC_{50}$ values were derived from experimental data by non-linear curve fitting (Prism Version 4; GraphPad Software, San Diego, Calif.).

Western blots: Cell cultures were rinsed twice with PBS and then lysed using RIPA buffer (100 mM Tris, 150 mM NaCl, 2 mM $CaCl_2$, 1% deoxycholic acid, 1% Triton X-100, 0.1% SDS, pH 7.5) containing PMSF (2 mM), NaF (500 mM), aprotinin (10 µg/ml), leupeptin (10 µg/ml) and vanadate (1 mM). Tissue samples were placed in ice-cold RIPA buffer and processed to lysates using a FastPrep homogenizer (QBiogene, Carlsbad, Calif.). Lysates were centrifuged at 15,000×g followed by assay for total protein using the bicinchoninic acid method (Pierce Biotechnology, Rockford, Ill.), then loaded at equal protein concentration onto gels for SDS-PAGE electrophoresis and Western blotting. For phosphorylated VE-cadherin detection blots were probed with primary antibody (Santa Cruz Biotechnology, Santa Cruz, Calif.) followed by a chemiluminescent detection system (Pierce Biotechnology). The same techniques were used to detect both phosphorylated and total ERK and Akt, except that primary antibodies were supplied by Cell Signaling Technology (Beverly, Mass.) and BD Biosciences (San Jose, Calif.), respectively.

Rodent MI model: All animal studies followed current "NIH Guidelines for the Use of Laboratory Animals" and were performed according to IACUC-approved protocols. Sprague-Dawley rats (275-300 g) were anesthetized using inhaled isoflurane after which chest walls were shaved and swabbed with iodine. Animals were then intubated and maintained on 2% isoflurane (delivered in 30% $O_2$/70% $N_2$), with optimal respiratory rate and stroke volumes set by a volume-controlled safety ventilator (Inspira Advanced Safety Ventilator; Harvard Apparatus, Holliston, Mass.). Body temperatures were maintained at 35-37° C. using heating pads and five-lead electrocardiograms established. For each animal, a left thoracotomy was performed at the third intercostal space, the heart was exposed and a suture snare tightened around the LAD at the point it appeared from beneath the left atrium. Ischemia was confirmed from blanching of the left ventricle (LV) as well as changes in ECG patterns. After the desired period of occlusion (60 min in the standard model), the suture snare was loosened to allow complete reperfusion (but retained in place using shallow sutures) and the chest closed in layers. Animals were weaned from isoflurane and mechanical respiration followed by administration of buprenorphine (0.01 mg/kg s.c.) and lactated Ringer's solution (1.5 ml i.p.). At the start of reperfusion, rats were randomized to treatment groups, and Compound I (at the desired dose, generally 0.5-5 mg/kg) or vehicle delivered as a single intravenous bolus (500 uL-1 ml volume) at the desired post-reperfusion time-point (generally 60 min).

For infarct size determination, LAD occlusion was repeated on each animal 24 hr after the initial occlusion. The ischemic zone (area-at-risk or AAR) was then delineated by i.v. injection of Evans blue dye (5 ml of a 10% saline solution containing 100 U/ml sodium heparin). The heart was explanted, atria and right ventricle trimmed free, and the LV (septal and free walls) frozen at −20° C. to induce rigor. After thawing on ice, the LV was subdivided into six 2 mm thick sections along the short axis using a metal form to guide dissection. Heart sections were stained for 20 min in 37° C. triphenyltetrazolium chloride (TTC, 2% in 0.04 M $K_2HPO_4$/0.17 M sucrose) to delineate viable from infarcted myocardium, fixed for 20 min in 10% formalin, then rinsed in saline. For each section, photographs were taken of both anterior and posterior surfaces and these images analyzed (by personnel blinded as to treatment identity) using a morphometric software package (Image Pro Plus; Media Cybernetics, Silver Spring, Md.). The following areas were calculated, based on their differing pixel densities: non-ischemic zone (Evans blue-stained), viable-but-ischemic zone (free of Evans blue but TTC-stained), and infarct-within-ischemic zone (free of both Evans blue and TTC stain). Area values for anterior and posterior views were averaged, and these values used to calculate the following $$AAR = \text{Viable-but-ischemic Area} + \text{Infarct Area} \quad \text{Equation 1}$$

$$\text{Total LV Area} = AAR + \text{Non-ischemic Area} \quad \text{Equation 2}$$

Porcine MI model: All animal studies followed current "NIH Guidelines for the Use of Laboratory Animals" and were performed according to IACUC-approved protocols. Farm swine (Landrace-Duroc cross, 32-41 kg) were acclimated for 1-3 weeks prior to study group randomization. On the day of surgery, animals (fasted overnight) were first administered aspirin, clopridogrel and nifedipine (650, 300 and 300 mg p.o., respectively), followed by atropine sulfate and telazol (0.05 and 7 mg/kg i.m., respectively). Anesthesia was then induced with ketamine and xylazine (25 mg/kg each i.m.) followed by intubation and maintenance on inhaled isoflurane; body temperature was maintained at 35-37° C. using heating pads. For each animal, the ventral neck was shaved and scrubbed with iodine, an arterial sheath inserted into the carotid artery, and under fluoroscopic guidance a guide catheter advanced to the coronary artery ostium. Angiographic images were used to guide angioplasty balloon placement (below the first major LAD bifurcation). After advancing through the guide catheter to the proper location, the balloon was inflated at a steady rate to a pressure sufficient to ensure complete occlusion of the LAD (verified by fluoroscopy), and occlusion maintained for 90 min. Blood pressure was monitored throughout the surgical procedure and adjusted as needed, and ECG monitored for arrhythmias as well as to confirm LAD occlusion. Lactated Ringer's solution was maintained as an i.v. drip (via the auricular vein), and heparin given to maintain an activated clotting time of ~300 seconds. Lidocaine (100 mg) and bretylium (100-250 mg) were introduced as needed to the i.v. drip to control ventricular arrhythmias, followed if needed by amiodarone (75 mg loading followed by 150 mg maintenance dose); defibrillation was used in the event of arrhythmias that did not acutely resolve. At the end of the ischemic period, the balloon was deflated and removed, and the ischemic area allowed to reperfuse (again verified by fluoroscopy). Catheters were removed, the arterial access ligated, the surgical area closed in layers and buprenorphine (0.01 mg/kg i.m.) administered.

Compound I (0.05-5 mg/kg) or vehicle were then administered 30 min post-reperfusion as a slow i.v. push (0.5 ml/kg over 2-3 min via the auricular vein). On Study Day 2 (24 hr post-LAD occlusion), a surgical plane of anesthesia was established with sodium pentobarbital, and the LAD exposed and occluded using a suture snare at the same level as previously. Evans blue dye (100 ml of 0.1% saline solution) was injected i.v. and allowed to circulate for 5 min prior to explanting the heart. Hearts were cut into approximately 1 cm short axis slices and TTC stained and photographed as described for the rodent MI model. Tissue morphometry was then performed (by personnel blinded as to treatment identity) again as described for the rodent MI model, except that area measurements were made not only for the total LV (septal and free wall) but also for free wall only.

Although the invention has been described with reference to the presently preferred embodiment, it should be understood that various modifications can be made without departing from the spirit of the invention. Accordingly, the invention is limited only by the following claims.

TABLE 1

PI3K isoform profiles. Kinase assays were performed to determine the $IC_{50}$ values against four isoforms of PI3K. Data are presented as the mean of triplicate values.

| Compound | $IC_{50}$ Value | | | |
|---|---|---|---|---|
| | PI3Kγ | PI3Kδ | PI3Kα | PI3Kβ |
| Compound II | 50 nM | 24 nM | 165 nM | 215 nM |
| Compound III | 85 nM | 64 nM | 1.2 μM | 107 nM |
| Compound I | 83 nM | 235 nM | 1.3 μM | 1.2 μM |
| LY29402 | 7.3 μM | 561 nM | 5.7 μM | 858 nM |
| Wortmannin | 55 nM | 103 nM | 99 nM | 147 mM |

TABLE 2

Compound I Profiling. Commercial services (Upstate USA, Charlottesville, VA; Invitrogen, Carlsbad, CA) were used to screen Compound I for inhibitory activity against a panel of 133 protein kinases. All kinases were of human origin unless denoted (m) for mouse or (r) for rat. Compound I and ATP final concentrations were 10 μM unless where indicated by an asterisk (*, denoting Compound I at 1 μM and ATP at the apparent Km). Data values are presented as Percent Control, where kinase reactions in the absence of Compound I score a value of 100. These data indicate that no kinase screened was inhibited with an apparent $IC_{50} \leq \mu M$.

| Kinase | Percent Control | Kinase | Percent Control | Kinase | Percent Control | Kinase | Percent Control |
|---|---|---|---|---|---|---|---|
| Abl (m) | 66 | EphA2 | 29 | MAPKAP-K2 | 107 | PKCi | 105 |
| Akt1* | 96 | EphA4 | 119 | MAPKAP-K3 | 93 | PKCC, | 99 |
| Akt2* | 103 | EphB2 | 56 | MEK1 | 94 | PKCγ | 75 |
| Akt3* | 98 | EphB4 | 68 | MEK2* | 94 | PKCθ | 73 |
| ALK4 | 91 | ErbB4 | 40 | Met | 41 | PKD2 | 37 |
| ALK | 48 | Fer | 80 | MINK | 88 | Plk3 | 97 |
| AMPK (r) | 88 | FGFR1 | 75 | MKK4 (m) | 57 | PRAK | 63 |
| Arg | 43 | FGFR2 | 73 | MKK6 | 75 | PRK2 | 83 |
| ASK1 | 105 | FGFR3 | 66 | MKK7b | 79 | Pyk2 | 68 |
| Aurora-A | 71 | FGFR4 | 94 | MSK1 | 92 | Ret | 57 |
| Axl | 76 | Fgr | 72 | MSK2 | 100 | ROCK-I | 93 |
| Blk (m) | 57 | Flt1 | 62 | MST1 | 107 | ROCK-II | 81 |
| Bmx | 58 | Flt3 | 80 | MST2 | 91 | Ron | 71 |
| BRK | 79 | Fms | 77 | NEK2 | 98 | Ros | 90 |
| BTK | 75 | Fyn | 54 | NEK6 | 97 | Rse | 93 |
| cKit | 96 | GSK3a | 62 | NEK7 | 99 | Rsk1 (r) | 86 |
| cRaf* | 98 | GSK3β | 70 | p70S6K | 91 | Rsk2 | 96 |
| CaMKII (r) | 90 | Hck | 67 | PAK2 | 87 | Rsk3 | 90 |
| CaMKIV | 87 | HIPK2 | 87 | PAK4 | 78 | SAPK2a | 55 |
| CDK1 | 54 | IGF-1R | 104 | PAR-1Ba | 93 | SAPK2b | 87 |
| CDK2 | 67 | IKKa | 100 | PDGFRa | 86 | SAPK3 | 98 |
| CDK2 | 77 | IKKβ | 68 | PDGFRβ | 86 | SAPK4 | 99 |
| CDK3 | 72 | IR | 81 | PDK1 | 90 | SGK | 95 |
| CDK5 | 82 | IRAK4 | 89 | Pim-1 | 70 | Syk | 76 |
| CDK6 | 83 | JAK3 | 99 | PKA | 93 | TAK1 | 65 |
| CDK7 | 82 | JNK1a1 | 80 | PKBa | 62 | TBK1 | 89 |
| CHK1 | 100 | JNK2a2 | 91 | PKBγ | 98 | TrkA | 57 |
| CHK2 | 75 | JNK3(r) | 64 | PKBβ | 103 | TrkB | 107 |
| CK1δ | 24 | KDR | 62 | PKCa | 90 | Yes | 30 |
| CK2* | 96 | Lck | 52 | PKCπ | 90 | ZAP-70 | 96 |
| CSK | 114 | Lyn (m) | 41 | PKCπI | 80 | ZIPK | 112 |
| cSrc | 53 | MAPK1 | 97 | PKCs | 69 | | |
| DDR2 | 88 | MAPK2 | 84 | PKCδ | 89 | | |
| EGFR | 99 | MAPK3* | 99 | PKCη | 72 | | |

What is claimed is:

1. A compound selected from a group consisting of Compound II and III:

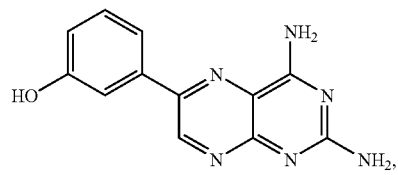

(II)

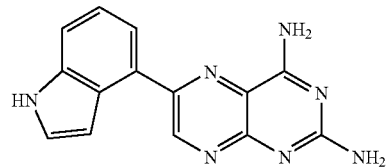

(III)

or pharmaceutically acceptable N-oxides, salts, or individual diastereomers thereof.

2. A pharmaceutical composition comprising a pharmaceutically effective amount of a compound and a pharmaceutically acceptable carrier according to claim 1.

3. A pharmaceutical composition, selected from the group consisting of 3-(2,4-diaminopteridin-6-yl)phenol and 6-(1H-Indol-4-yl)pteridine-2,4-diamine, or a pharmaceutically acceptable salt thereof, and a pharmaceutically acceptable carrier therefor.

4. The pharmaceutical composition of claim 3, further comprising cyclodextrin.

5. The pharmaceutical composition of claim 4, wherein the cyclodextrin is β-cyclodextrin.

6. The pharmaceutical composition of claim 4, wherein the cyclodextrin is a sulfobutyl ether of β-cyclodextrin.

7. The pharmaceutical composition of claim 3, further comprising citric acid.

* * * * *